United States Patent
Kasic, II

(10) Patent No.: US 10,265,058 B2
(45) Date of Patent: *Apr. 23, 2019

(54) SYSTEMS, DEVICES, COMPONENTS AND METHODS FOR DISPLACING AND REPOSITIONING THE ESOPHAGUS AWAY FROM THE HEART DURING ATRIAL ABLATION SURGICAL PROCEDURES

(71) Applicant: DNP Biomed, LLC, Boulder, CO (US)

(72) Inventor: James F Kasic, II, Boulder, CO (US)

(73) Assignee: DNP Biomed, LLC

( * ) Notice: Subject to any disclaimer, the term of this patent is extended or adjusted under 35 U.S.C. 154(b) by 0 days.

This patent is subject to a terminal disclaimer.

(21) Appl. No.: 15/603,176

(22) Filed: May 23, 2017

(65) Prior Publication Data

US 2017/0252027 A1    Sep. 7, 2017

Related U.S. Application Data

(63) Continuation-in-part of application No. 14/887,313, filed on Oct. 19, 2015, now Pat. No. 9,668,720.

(51) Int. Cl.
  *A61B 17/00* (2006.01)
  *A61B 17/02* (2006.01)
  (Continued)

(52) U.S. Cl.
  CPC ...... *A61B 17/00234* (2013.01); *A61B 5/0071* (2013.01); *A61B 17/0218* (2013.01);
  (Continued)

(58) Field of Classification Search
  CPC .............. A61B 18/14; A61B 17/00234; A61B 17/0218; A61B 5/0071; A61B 2090/3966;
  (Continued)

(56) References Cited

U.S. PATENT DOCUMENTS

| 6,067,990 A | * | 5/2000 | Kieturakis ......... A61B 17/0218 128/898 |
| 6,438,400 B1 | | 8/2002 | Beard et al. |

(Continued)

OTHER PUBLICATIONS

C. Palaniswamy et al., Effectiveness of Egaphageal Meshanical Deviation during AF Ablation, PO01-83, Hearty Rhythm Society, May 13, 2015.

(Continued)

*Primary Examiner* — Pedro Philogene
(74) *Attorney, Agent, or Firm* — Woods Patent Law, P.A.

(57) ABSTRACT

Disclosed are various embodiments of systems, devices, components and methods for re-positioning or displacing a patient's esophagus a safe distance away from the patient's heart during an atrial ablation surgical procedure. An esophageal displacement catheter is disclosed that is configured to reposition a patient's esophagus 20 mm or more away from an ablation location in the patient's heart. A distendable section of the catheter is configured such that portions of a first pulling member extend sufficiently far away from joints located in the distendable section when the first pulling member is in a retracted position to permit the distendable section to assume a deployed and distended configuration. At least one flexible deformable or distendable member, sheath or covering is configured to be disposed over and cover the portions of the first pulling member extending away from the joints when the distendable section is the deployed and distended configuration. One or more balloons may also be incorporated into the catheter to enlarge controllably the diameter of the distendable section.

27 Claims, 24 Drawing Sheets

(51) Int. Cl.
*A61B 5/00* (2006.01)
*A61B 18/14* (2006.01)
*A61B 18/00* (2006.01)
*A61B 90/00* (2016.01)

(52) U.S. Cl.
CPC .......... *A61B 18/14* (2013.01); *A61B 18/1492* (2013.01); *A61B 2017/00084* (2013.01); *A61B 2017/00309* (2013.01); *A61B 2017/00323* (2013.01); *A61B 2018/00351* (2013.01); *A61B 2018/00577* (2013.01); *A61B 2018/00791* (2013.01); *A61B 2018/00982* (2013.01); *A61B 2090/3966* (2016.02)

(58) Field of Classification Search
CPC ...... A61B 18/1492; A61B 2017/00084; A61B 2017/00309; A61B 2017/00323; A61B 2018/00351; A61B 2018/00577; A61B 2018/00791; A61B 2018/00982
USPC .................. 606/21–26, 1, 32, 34, 41, 191; 600/144–151, 120, 289; 607/112, 129, 607/133, 135
See application file for complete search history.

(56) References Cited

U.S. PATENT DOCUMENTS

| | | | |
|---|---|---|---|
| 7,621,908 B2 | 11/2009 | Miller | |
| 7,819,817 B2 | 10/2010 | Rahn | |
| 8,224,422 B2 | 7/2012 | Mottola et al. | |
| 8,273,016 B2 | 9/2012 | O'Sullivan | |
| 8,454,588 B2* | 6/2013 | Rieker | A61M 25/0147 606/191 |
| 8,968,332 B2* | 3/2015 | Farritor | A61B 1/00158 606/130 |
| 9,668,720 B2* | 6/2017 | Kasic, II | A61B 17/0218 |
| 2004/0138700 A1 | 7/2004 | Cooper et al. | |
| 2007/0118097 A1 | 5/2007 | Miller | |
| 2007/0135803 A1* | 6/2007 | Belson | A61B 1/00154 606/1 |
| 2007/0225701 A1 | 9/2007 | O'Sullivan | |
| 2008/0033415 A1 | 2/2008 | Rieker et al. | |
| 2008/0215047 A1 | 9/2008 | Calabro et al. | |
| 2008/0228171 A1 | 9/2008 | Kugler et al. | |
| 2009/0240335 A1 | 9/2009 | Arcenio et al. | |
| 2010/0030098 A1 | 2/2010 | Fojtik | |
| 2010/0168864 A1 | 7/2010 | White et al. | |
| 2010/0179537 A1 | 7/2010 | Rashidi | |
| 2015/0245829 A1 | 9/2015 | Fojtik | |
| 2016/0317138 A1 | 11/2016 | Kasic | |

OTHER PUBLICATIONS

Lemola et al., Computed Tomographic Analysis of the Anatomy of the Left Atrium, Circulation, 2004, pp. 3655-3660.

Musat et al., Computational Method to Predict Esophageal Temperature Elevations During Pulmonary Vein Isolation, PACE, vol. 33, Issue 10, 2010, pp. 1239-1248.

J. Koruth et al., Mechanical Esophageal Displacement During Catheter Ablation for Atrial Fibrillation, Jorn. Cardiovascular Electrophysiology, vol. 23, Issue 2, pp. 147-154.

Singh et al., Esophageal Injury and Temperature Monitoring During Atrial Fibrillation Ablation, Circ Arrhythmia Electrophysiol, Aug. 2008, pp. 162-168.

* cited by examiner

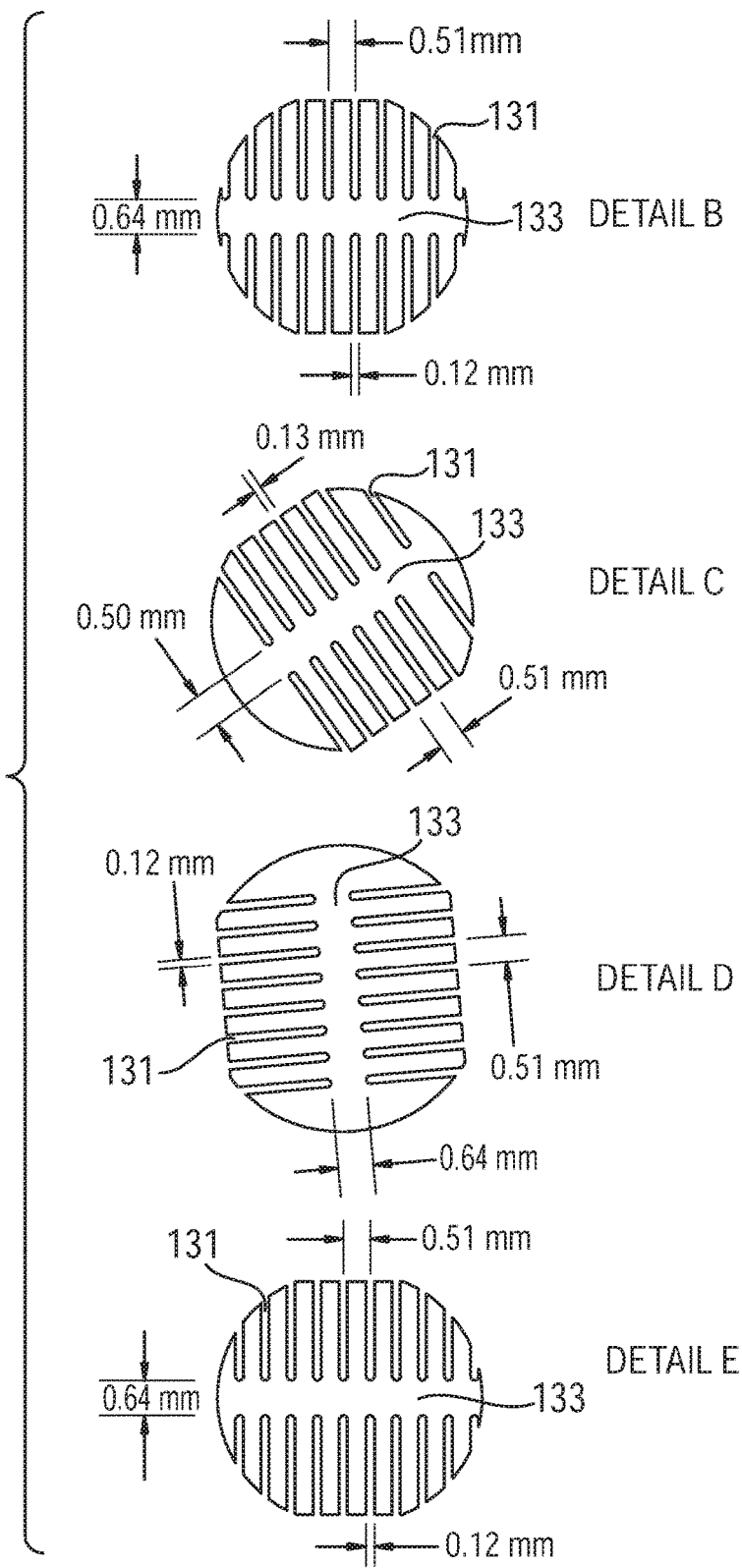

SYSTEMS, DEVICES, COMPONENTS AND METHODS FOR DISPLACING AND REPOSITIONING THE ESOPHAGUS AWAY FROM THE HEART DURING ATRIAL ABLATION SURGICAL PROCEDURES

RELATED APPLICATION

This application claims priority and other benefits from, and is a continuation-in-part of, U.S. patent application Ser. No. 14/887,313 to Kasic entitled "Systems, Devices, Components and Methods for Displacing and Repositioning the Esophagus Away from the Heart during Atrial Ablation Surgical Procedures" filed on Oct. 19, 2015, now U.S. Pat. No. 9,668,720 issued on Jun. 6, 2017 ("the 720 patent"). The entirety of the '720 patent is hereby incorporated by reference herein.

FIELD OF THE INVENTION

Various embodiments of the invention described herein relate to the field of systems, devices, components, and methods for displacing or repositioning a patient's esophagus away from the patient's heart during an atrial ablation or other surgical procedure.

BACKGROUND

Catheter ablation is commonly employed to treat atrial fibrillation, where errant electrical conductivity pathways in a patient's heart are burned or ablated with the tip of an ablation catheter that is positioned within the patient's atrium during a cardiac ablation surgical procedure. A significant risk in such a procedure is burning or ablating through a wall of the patient's atrium and then into the patient's esophagus, or otherwise damaging or overheating esophageal tissue. Indeed, burning or ablating the patient's esophagus can result in near-immediate death. See, for example, "Damage to the Esophagus After Atrial Fibrillation Ablation—Just the Tip of the Iceberg? High Prevalence of Mediastinal Changes Diagnosed by Endosonography" to Zellerhoff et al., Circulation: Arrhythmia and Electrophysiology. 2010; 3:155-159, Apr. 20, 2010. Zellerhoff et al. describe structural changes in the mediastinum resulting from PV isolation and ablation, which were only visible by endosonography, and which occurred in 27% of the patients studied.

Mechanical esophageal displacement of the esophagus away from the heart during a cardiac ablation surgical procedure is therefore highly desirable so that in the event a patient's atrial wall is penetrated during the procedure the esophagus will not be burned or ablated. See "Mechanical Esophageal Displacement during Catheter Ablation for Atrial Fibrillation" by Koruth et al. Journal of Cardiovascular Electrophysiology, Vol. 23, No. 2, February, 2012.

Various devices and methods have been proposed to displace or reposition a patient's esophagus during atrial ablation surgical procedures, many of which suffer from various shortcomings.

What is needed is an esophageal displacement or re-positioning device that is relatively quick and easy to use, and that is capable of reliably re-positioning a patient's esophagus a safe distance away from the patient's heart during a cardiac ablation surgical procedure.

SUMMARY

In one embodiment, there is provided an esophageal displacement catheter comprising a catheter body having a longitudinal axis associated therewith, the catheter body comprising a distal end, a proximal end, at least one lumen, and a distendable section having sidewalls, the lumen extending between at least portions of the proximal and distal ends, the catheter body being configured to assume an at least partially flexible or limp configuration along at least portions of the longitudinal axis when the catheter body is in a relaxed or non-active configuration, a catheter manipulation mechanism disposed at or near the proximal end of the catheter body, at least a first pulling member disposed at least partially within the catheter and the lumen, the first pulling member comprising a distal portion operably connected to or near a distal end of the catheter body and a proximal portion operably connected to the catheter manipulation mechanism such that a user can tighten and relax the pulling member using the catheter manipulation mechanism, and at least one elastic flexible deformable or distendable member, sheath, layer or covering disposed over at least portions of the distendable section, wherein the distendable section comprises a plurality of substantially rigid sections interconnected by a plurality of joints disposed along the distendable section, the joints and substantially rigid segments being configured to permit the distendable section to deflect away from the longitudinal axis and assume a distended configuration when the first pulling member is pulled or retracted sufficiently far towards the proximal end of the catheter body using the catheter manipulation mechanism, the distendable section further being configured such that portions of the first pulling member extend sufficiently far away from the joints when the first pulling member is in a retracted position to permit the distendable section to assume a deployed and distended configuration, and the at least one flexible deformable or distendable member, sheath or covering is configured to be disposed over and cover the portions of the first pulling member extending away from the joints when the distendable section is the deployed and distended configuration, the catheter being configured to displace and reposition an esophagus of a patient at least 20 mm away from the patient's heart when the distendable section is in the deployed and distended configuration.

In another embodiment, there is provided a method of displacing a portion of an esophagus of a patient away from the patient's heart with an esophageal displacement catheter, the catheter comprising a catheter body having a longitudinal axis associated therewith, the catheter body comprising a distal end, a proximal end, at least one lumen, and a distendable section having sidewalls, the lumen extending between at least portions of the proximal and distal ends, the catheter body being configured to assume an at least partially flexible or limp configuration along at least portions of the longitudinal axis when the catheter body is in a relaxed or non-active configuration, a catheter manipulation mechanism disposed at or near the proximal end of the catheter body, at least a first pulling member disposed at least partially within the catheter and the lumen and comprising a distal portion operably connected to or near a distal end of the catheter body and a proximal portion operably connected to the catheter manipulation mechanism such that a user can tighten and relax the pulling member using the catheter manipulation mechanism, and at least one elastic flexible deformable or distendable member, sheath, layer or covering disposed over at least portions of the distendable section, the distendable section comprising a plurality of substantially rigid sections interconnected by a plurality of joints disposed along the distendable section, the joints and substantially rigid segments being configured to permit the distendable section to deflect away from the longitudinal axis and assume a distended configuration when the first pulling member is retracted or pulled sufficiently far towards the proximal end of the catheter body using the catheter manipulation mechanism, the distendable section further being configured such that portions of the first pulling member extend sufficiently far away from the joints when the first pulling member is in a retracted position to permit the distendable section to assume a deployed and distended configuration, and the at least one flexible deformable or distendable member, sheath or covering is configured to be disposed over and cover the portions of the first pulling member extending away from the joints when the distendable section is the deployed and distended configuration, the catheter being configured to displace and reposition an esophagus of a patient at least 20 mm away from the patient's heart when the distendable section is in the deployed and distended configuration, the method comprising inserting the distal end of the catheter body in the patient's nose or mouth, inserting and positioning the distal end of the catheter into the patient's esophagus, and causing the first pulling member to retract in the direction of the proximal end of the catheter body such that the distendable section is deployed, the distendable section assumes the distended configuration, and the distendable section positions the patient's esophagus at least 20 mm away from the patient's heart.

Further embodiments are disclosed herein or will become apparent to those skilled in the art after having read and understood the specification and drawings hereof.

BRIEF DESCRIPTION OF THE DRAWINGS

Different aspects of the various embodiments will become apparent from the following specification, drawings and claims in which:

FIG. 9(e) shows details C, D, E and F of distendable section 110 of esophageal displacement and repositioning catheter 10 shown in FIGS. 9(c) and 9(d);

The drawings are not necessarily to scale. Like numbers refer to like parts or steps throughout the drawings.

DETAILED DESCRIPTIONS OF SOME EMBODIMENTS

Figure 1:
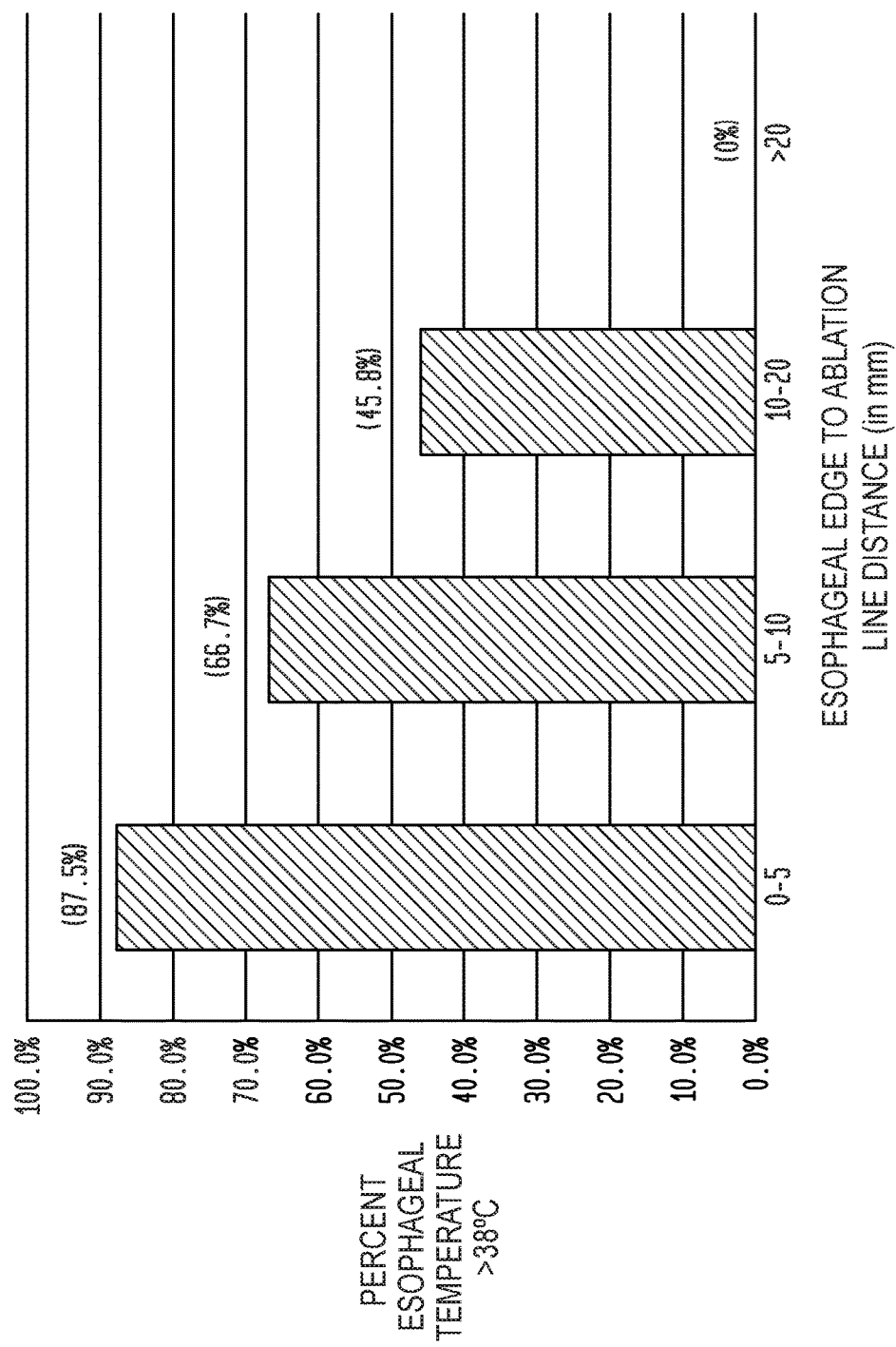
FIG. 1 shows the relationship between esophageal temperature and esophageal edge to ablation line distance in millimeters.

Described herein are various embodiments of systems, devices, components and methods for repositioning and displacing a patient's esophagus away from the patient's heart during an atrial ablation surgical procedure.

The esophagus is in close proximity to the posterior wall of the left atrium, which renders it susceptible to thermal injury during radiofrequency (RF) ablation procedures for atrial fibrillation (AF). Real-time assessment of esophageal position and temperature (T°) during pulmonary vein (PV) isolation has not been extensively explored. See "*Computational Method to Predict Esophageal Temperature Elevations During Pulmonary Vein Isolation*" to Musat, M. D. et al., Pacing and Clinical Electrophysiology, Volume 33, Issue 10, pages 1239-1248, October 2010. Atrial fibrillation ablation (AF ablation) can include isolation of the left or right pulmonary veins by applying ablation energy at their junction with the atrium.

The Centers for Disease Control (CDC) estimates that 12 million people in the US have atrial fibrillation (AF). Worldwide, about 260,000 people are treated by AF ablation each year. In up to 1% of these cases, atria-esophageal fistulas develop because of overheating and damage that have occurred to the esophagus during the AF ablation procedure. Overheating and damage to the esophagus can occur when heart tissue is burned or ablated through during the AF ablation procedure. Between 70 and 100% of patients who develop atrio-esophageal fistulas as a consequence of AF ablation die. Moreover, esophageal injury of some sort occurs in up to 36% of AF ablation procedures. See "*Computed Tomographic Analysis of the Anatomy of the Left Atrium*" to Lemola et al., Circulation, 2004; and "Esophageal Injury and Temperature Monitoring" to Singh et al., Circulation, October, 2008. See also Zellerhoff et al., infra.

Temperature sensors disposed in the esophagus have been used with varying success during AF ablation procedures, but can be unwieldy, slow to react, have small sensing areas, or be located away from the critically important trailing edge of the esophagus, which is located closest to the site where AF ablation occurs and is therefore most susceptible to damage and overheating.

Various studies have indicated there is little to no heating of the esophagus during an AF ablation procedure when the esophagus is repositioned or displaced at least 20 mm away from the ablation site. See, for example, "*Effectiveness of Esophageal Mechanical Deviation during AF Ablation*," C. Palaniswamy et al., PO01-83, Hearty Rhythm Society, May 13, 2015.

As a result, solutions have focused on moving the esophagus away from the patient's heart during AF ablation procedures using devices such as wires, balloons and catheters. Such devices, however, often suffer from one or more problems, including excessive cost, an inability to achieve the amount of deflection, displacement or repositioning of the esophagus away from the heart required to prevent burning damage or injury to the esophagus, trauma to the oropharynx, and/or an inability to rotate or reposition, or difficulty in rotating or repositioning, the device in the esophagus once it has been inserted in the esophagus and deployed. For example, many balloon- and catheter-based devices are incapable of transmitting torque efficiently or adequately between the proximal and distal ends thereof if fluoroscopic or other suitable imaging techniques reveal that the device must be rotated in the esophagus to achieve the desired amount of esophageal displacement away from the heart. Moreover, the location of the trailing edge of the esophagus (which is closest to the ablation site and therefore most susceptible to burning or injury) is typically not taken into account by the various esophageal displacement devices that have been developed. See "Mechanical Esophageal Displacement During Catheter Ablation for Atrial Fibrillation," J. Koruth et al., Journal of Cardiovascular Electrophysiology, Volume 23, Issue 2, pages 147-154, February 2012.

The various embodiments disclosed and described herein provide solutions to at least some of the problems outlined above.

Referring now to FIG. 1, there are shown measured relationships between esophageal temperature and an esophageal edge-to-ablation line distance in millimeters. FIG. 1 is adapted from C. Palaniswamy et al., Heart Rhythm Scientific Sessions, 2015, in Boston, Mass. (see above), and illustrates the importance of re-positioning or displacing the esophagus, generally in a lateral direction instead of a posterior direction, and typically 20 mm or more away from the ablation site during an AF ablation procedure. FIG. 1 illustrates the percentage of patients where the edge of the esophagus was heated to a temperature exceeding 38 degrees Celsius as a function of distance between the esophagus and the ablation site. As shown, no patients experienced heating of the edge of the esophagus above 38 degrees Celsius when the distance between the edge of the esophagus and the ablation site exceeded 20 mm.

Figure 2A:
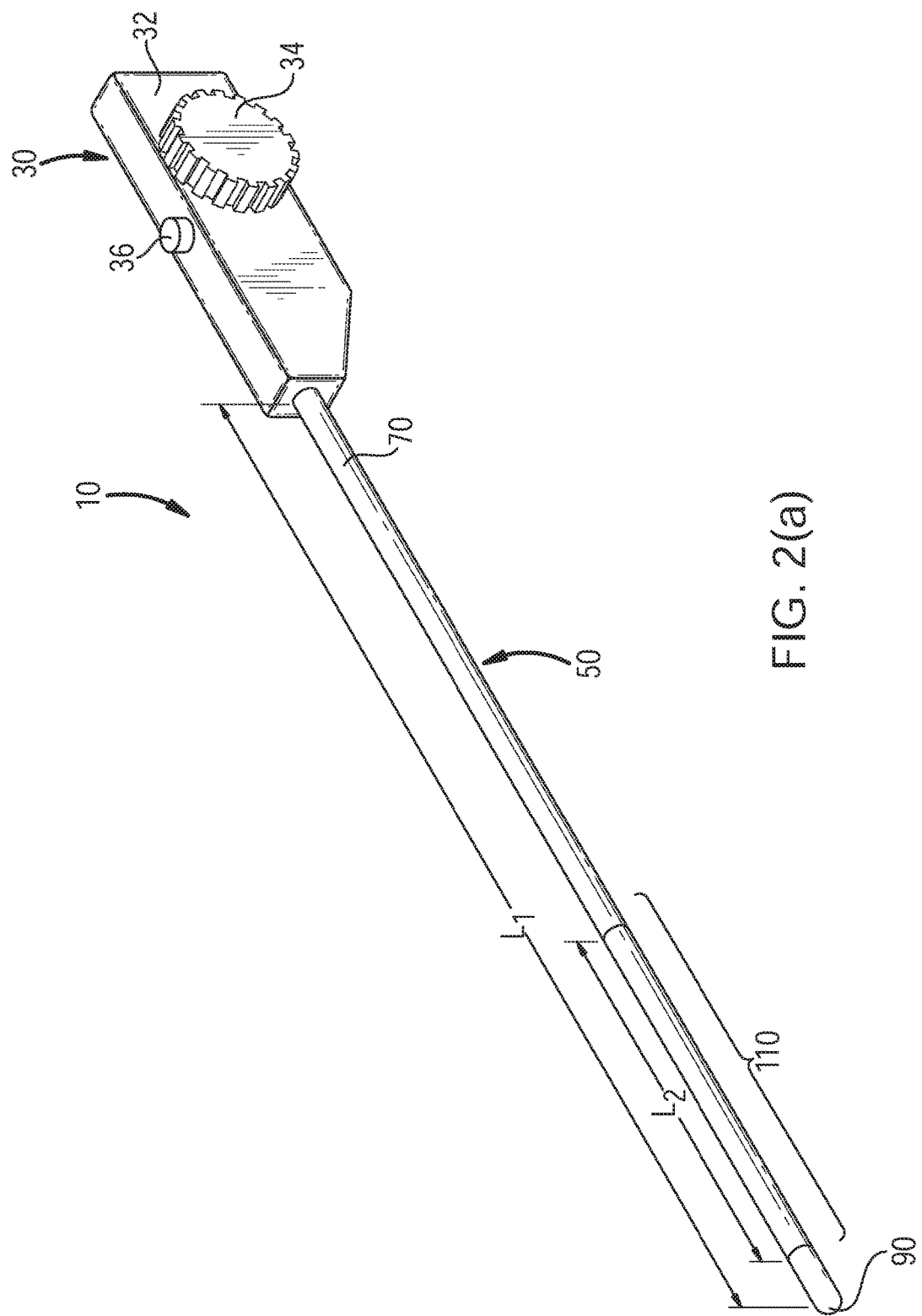
FIG. 2(a) shows a top perspective view of one embodiment of an esophageal displacement and repositioning catheter 10 in a resting or non-distended or non-deployed position.

FIG. 2(a) shows a top perspective view of one embodiment of an esophageal displacement and repositioning catheter 10 in a resting or non-distended position. As shown, catheter 10 comprises catheter body 50 having proximal end 70 and distal end 90, distendable section 110 of catheter body 50, and catheter manipulation handle 30. Catheter body 50 is further characterized in having overall length L1, and length L3 associated with distendable section 110. In one embodiment, catheter manipulation mechanism or handle 30 comprises housing 32, pulling member tightening and loosening dial 34, and ratchet locking and unlocking button 36. Other types of pulling member tightening and loosening mechanisms known to those skilled in the art are also contemplated, such as triggers, levers, and so on.

Figure 2B:
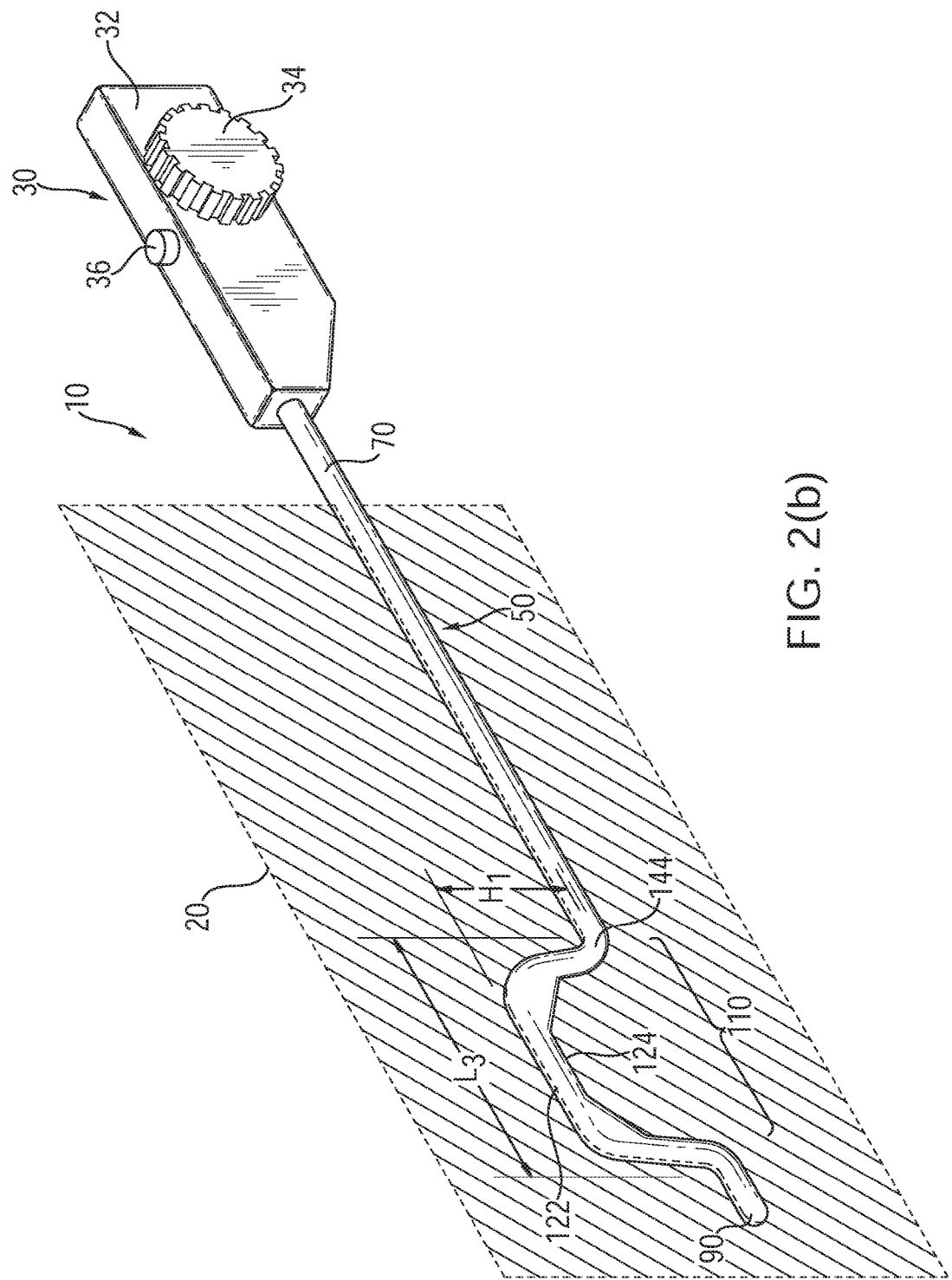
FIG. 2(b) shows a top perspective view of the esophageal displacement and repositioning catheter 10 of FIG. 2(a) in an active, distended or deployed configuration.

FIG. 2(b) shows a top perspective view of esophageal displacement and repositioning catheter 10 of FIG. 2(b), where distendable section 110 is in an active or distended position, and where a user or health care provider has employed handle 30 and dial 34 to retract a first pulling member 136 (not shown in FIGS. 2(a) through 2(c), but described in further detail below and in other Figures) disposed within catheter body 50 thereby to cause distendable section 110 to assume the distended configuration shown in FIG. 2(b). As shown, distendable section 110 comprises a leading edge 122, a trailing edge 124, a first height H1, a length L3, and an elastic, flexible, stretchable, and/or distendable member, sheath, covering, or outer layer 144 disposed over at least portions of distendable section 110, more about which is said below.

Catheter body 50 of FIGS. 2(a) through 2(c) also comprises at least a first lumen 40 (also not shown in FIGS. 2(a) through 2(c), but described in further detail below and in other Figures), which is configured to accommodate first pulling member 136, and which extends between at least portions of proximal and distal ends 70 and 90. In one embodiment, the at least first pulling member 136 is disposed at least partially within catheter body 50 and lumen 40. A plurality of substantially rigid segments located in or on a distendable section of catheter 10, where the segments are serially connected to one another by flexible joints, are disposed in distendable section 110 (more about which is said below and shown in other Figures). In one embodiment, each of such segments is rotatable through a prescribed range of angles, and the segments are configured to rotate within substantially a same plane thereby to transmit rotational torque efficiently through distendable section 110. Other rigid sections can be connected proximally from distendable section 110 to handle 30 or proximal end 70 thereby to transmit rotational torque efficiently from proximal end 70 to distal end 90 through distendable catheter body 50.

Figure 2C:
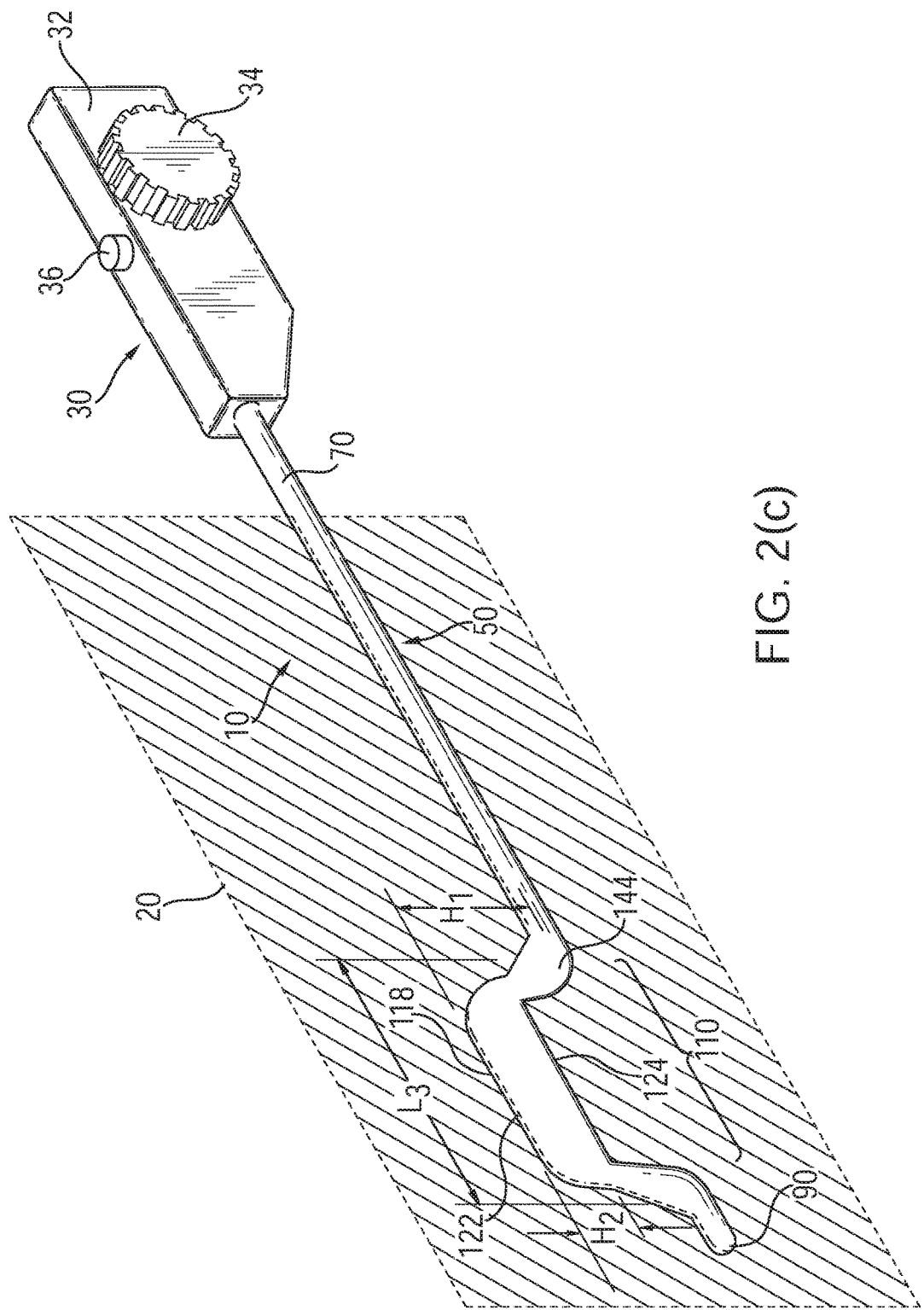
FIG. 2(c) shows a top perspective view of another embodiment of an esophageal displacement and repositioning catheter 10 in an active, distended or deployed configuration.

Additionally, shown in FIGS. 2(b) and 2(c) is imaginary or single plane 20, which bisects catheter body 50 and distendable section 110 when distendable section 110 is distended, deployed or activated. Distendable section 110 comprises a plurality joints and is configured to deflect away from a longitudinal axis associated with the remaining undeflected portion of catheter body 50. In one embodiment of the distended configuration, distendable section 110 bends and deflects substantially within single plane 20 along the plurality of joints when pulling member 136 is pulled towards proximal end 70 of catheter body 50. In one embodiment, distendable section 110 and catheter body 50 may further be configured to rotate substantially within single plane 20 when the proximal end 70 of catheter body 50 or catheter manipulation mechanism 30 is rotated by a user. In one embodiment, catheter body 50 is configured such that distendable section 110 is configured to assume a distended configuration (shown in FIGS. 2(b) and 2(c)) suitable for displacing and repositioning an esophagus of a patient a suitable distance away from the patient's heart (e.g., 20 mm or more away from the patient's heart) when the pulling member is in an active or distended position within lumen 40 and catheter body 50 as pulling member 136 is tightened, for example, by the user manipulating the catheter manipulation mechanism or handle 30. In addition, and in one embodiment, catheter 50 is configured such that a torsional and rotational force applied to proximal end 70 of catheter body 50 or catheter manipulation mechanism 30 by the user results in a rotation of proximal end 70 of catheter body 50 through a prescribed angle determined by the user, and may also be configured such that torsional force is transmitted efficiently through catheter body 50 and distendable section 110 such that distendable section 110 also rotates substantially through the prescribed angle when the torsional and rotational force is applied by the user. In some embodiments, distendable section 110 may be configured to assume a distended configuration suitable for displacing and repositioning an esophagus of a patient about 20 mm, about 25 mm, about 30 mm, about 35 mm, and/or about 40 mm away from the patient's heart). Other distances D2 away from the heart are also contemplated (see, e.g., FIG. 3(b)).

Thus, in the embodiments shown in FIGS. 2(a) through 2(c), catheter 10 is configured to be substantially straight and/or at least partially flexible or limp between proximal and distal ends 70 and 90 when first pulling member 136 is in a resting or non-distension position within lumen 40, and catheter 10 is further configured such that distendable section 110 thereof assumes a distended configuration suitable for displacing and repositioning an esophagus of a patient away from the patient's heart when first pulling member 136 is in an active or distended position within lumen 40 and catheter body 50 as first pulling member 136 is pulled by a user using, by way of non-limited example, catheter manipulation mechanism or handle 30. In addition, and in one embodiment, catheter 10 is configured such that a rotational or torsional force applied to proximal end 70 of catheter body 50 or handle 30 results in a rotation of proximal end 70 of catheter body 50 through a prescribed number of degrees, and may further be configured to result in such torsional force being transmitted efficiently through catheter body 50 and distendable section 110 such that distal end 90 of catheter body 50 also rotates substantially through the prescribed number of degrees when the such force is applied by a user or health care provider, distendable section and catheter body 50 rotating together substantially in single plane 20.

Note that depending on the particular configuration of distendable catheter 10 that is to be employed, catheter body 50 and catheter sidewalls 54 may be formed from any of a number of suitable biocompatible materials, including, but not limited to, silicone, silicone-based materials, medical-grade silicone, rubber silicone materials, latex-based materials, latex, rubber-based materials, rubber, rubber latex materials, urethane-based materials, polyurethane-containing materials, suitably flexible polyethylene-containing materials, polyethylene terephthalate (PET)-containing materials, polyisoprene-containing materials, polypropylene, fluoroplastic, polymers, elastomers, thermoplastic elastomers, and combinations and mixtures of the foregoing. Other materials that are biocompatible and suitably flexible, and that are otherwise safe for use inside the human body, are also contemplated.

First and second pulling members may be formed from any of a number suitable materials, including, but not limited to, wire, metal wire, alloy wire, stainless steel wire, stranded wires, braided wires, KEVLAR®, carbon fibers, wound, braided or stranded polymer fibers, and the like.

FIG. 2(c) shows a top perspective view of another embodiment of an esophageal displacement and repositioning catheter 10 in an active or distended position. As shown, catheter 10 comprises catheter body 50 having proximal end 70 and distal end 90, distendable section 110 of catheter body 50, and catheter manipulation handle 30. In one embodiment, catheter body 50 is further characterized in having length L3 associated with distendable section 110, and heights H1 and H2 associated with distendable section 110. Handle 30 comprises housing 32, pulling member tightening and loosening dial 34, and ratchet locking and unlocking button 36. In the embodiment shown in FIG. 2(c), distendable section 110 is in an active or distended position, where a user or health care provider has employed handle 30 and dial 34 to retract a first pulling member 136 (not shown in FIG. 2(c), but described in further detail below and in other Figures) disposed within catheter body 50 thereby to cause distendable section 110 to assume the distended configuration shown in FIG. 2(c). As shown, distendable section 110 comprises a leading edge 122 and a trailing edge 124, a first height H1, and a second height H2. In comparison to the embodiment of FIGS. 2(a) and 2(b), it will be seen that distendable section 110 of the embodiment shown in FIG. 2(c) features a thickened or greater diameter distendable section 110, where leading edge 122 is separated from trialing edge 124 by height H2.

It has been discovered that a thickened or greater diameter distendable section 110 can help pull at least portions of the trailing edge 202 of esophagus 200 (not shown in FIG. 2(c), but described below and shown in other Figures), towards distendable section 110 and therefore a further distance away from a patient's atrium or heart during an AF ablation procedure than can be achieved with the embodiment of catheter 10 shown in FIGS. 2(a) and 2(b).

Referring now to FIGS. 2(a) through 2(c), and in some embodiments, esophageal displacement catheter 10 is characterized by the following dimensions and/or specifications: (a) prescribed ranges of angles between sections of distendable section 110 range between about 40 degrees and about 90 degrees, between about 45 degrees and about 85 degrees, between about 50 degrees and about 80 degrees, between about 55 degrees and about 75 degrees, and/or between about 60 degrees and about 70 degrees; (b) first length L1 between proximal and distal ends 70 and 90 of catheter body 50 ranges between about 200 mm and about 600 mm, between about 250 mm and about 550 mm; between about 300 mm and about 500 mm, and other lengths; (c) second length L2 of distendable section 110 ranges between about 100 mm and about 300 mm, between about 125 mm and about 275 mm, between about 150 mm and about 250 mm, and other lengths; (d) third length L3 of distendable section 110 ranges between about 80 mm and about 250 mm (where in some embodiments about 100 mm is a preferred third length L3); (e) first height H1 of distendable section 110 ranges between about 40 mm and about 140 mm (where in some embodiments about 80 mm is a preferred first height H1), and second height H2 of distendable section 110 ranges between about 20 mm and about 80 mm, between about 30 mm and about 70 mm, and/or between about 35 mm and about 65 mm. Other dimensions and specifications that will now become apparent to those skilled in the art after having read and understood the specification and drawings hereof are also contemplated.

Figure 3A:
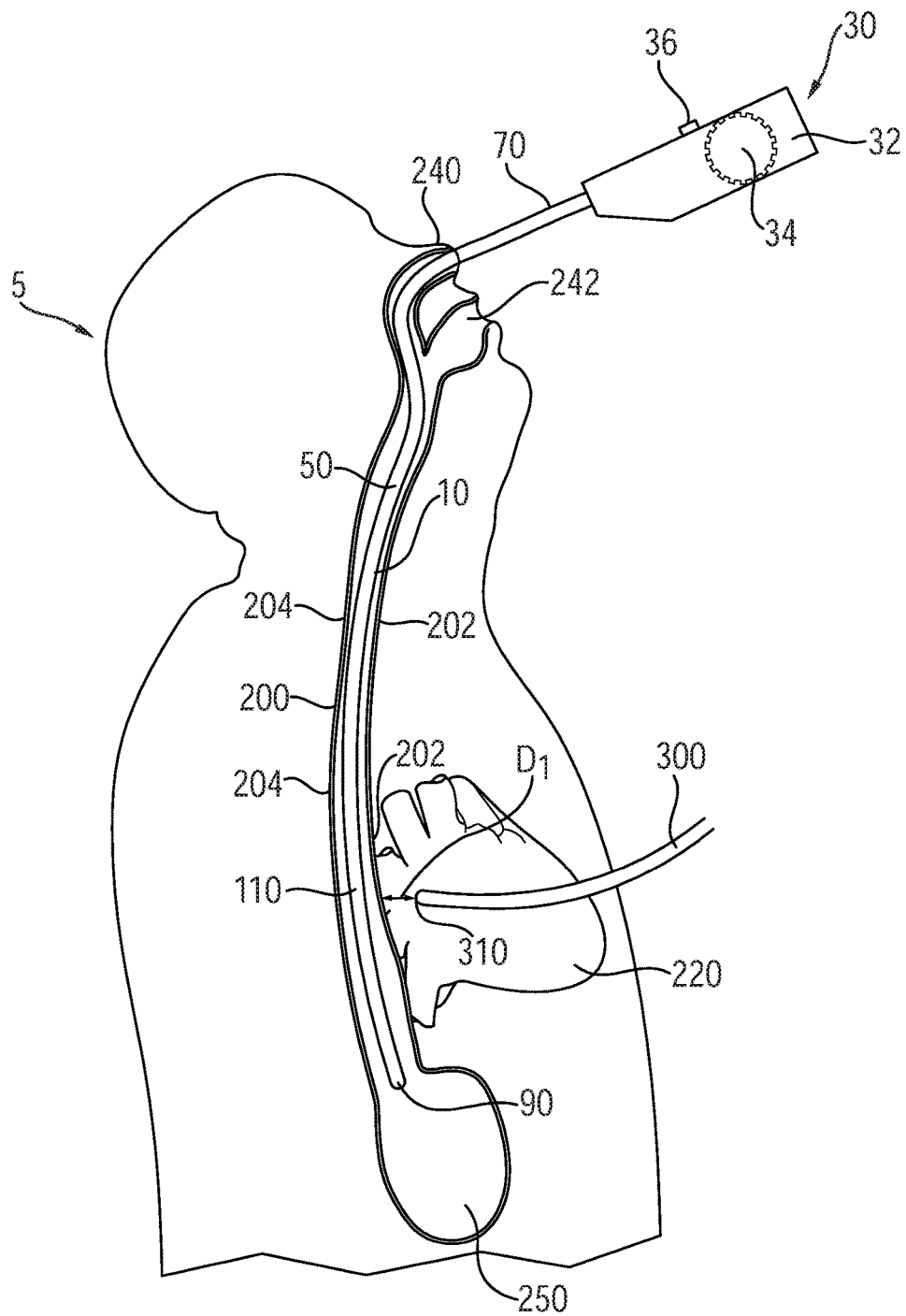
FIG. 3(a) shows a cross-sectional view of one embodiment of an esophageal displacement and repositioning catheter 10 positioned in esophagus 200 of patient 5, where catheter 10 is in a resting, or on-distended or non-deployed configuration.

FIG. 3(a) shows a cross-sectional view of one embodiment of esophageal displacement and repositioning catheter 10 positioned in esophagus 200 of a patient 5, where catheter 10 is in a resting, non-distended or inactive position in patient 5. Ablation tip 310 of AF ablation catheter 300 is positioned in one of the patient's atria. Trailing edge 202 of esophagus 200 is located in close proximity to, or distance D1 away from, heart 200 and ablation tip 310. Leading edge 204 of esophagus 200 is located further away from ablation tip 310 than distance D1. Catheter 10 can be configured such that catheter body 50 has length L1 such that distal end 90 is configured to enter stomach 250, or is configured not to enter stomach 250. Indeed, catheter 10 can be configured to have lengths L1, L2, L3, L4, H1 and H2 selected such that catheter 10 may be employed successfully in patients of different ages or who have differing esophageal, nose, mouth, and stomach dimensions and morphologies.

In one embodiment, catheter body 50 has a diameter of about 6 mm or less so that it can be inserted through a patient's nose, and further such that the patient need not undergo general anesthetic during the AF ablation procedure (as is typically done when an esophageal catheter is placed through the patient's mouth into esophagus 200). Other diameters of catheter body 50 are also contemplated, such as by way of non-limiting example about 4 mm, about 5 mm, about 7 mm, about 8 mm, and so on.

In addition, esophageal displacement catheter 10 may comprise at least one radio-opaque, acoustically-opaque, or other type of marker disposed along catheter body 50 indicative of at least one of a first position of distal end 90 of catheter 10 in patient 5's esophagus 200 and a second position of distendable section 110 in the patient 5's esophagus 200. In still other embodiments, esophageal displacement catheter 10 may comprise one or more temperature sensors, ultrasonic transducers, radio- or acoustically-opaque markers, and/or navigation sensors disposed in distendable section 110 or other portions of catheter 10.

Figure 3B:
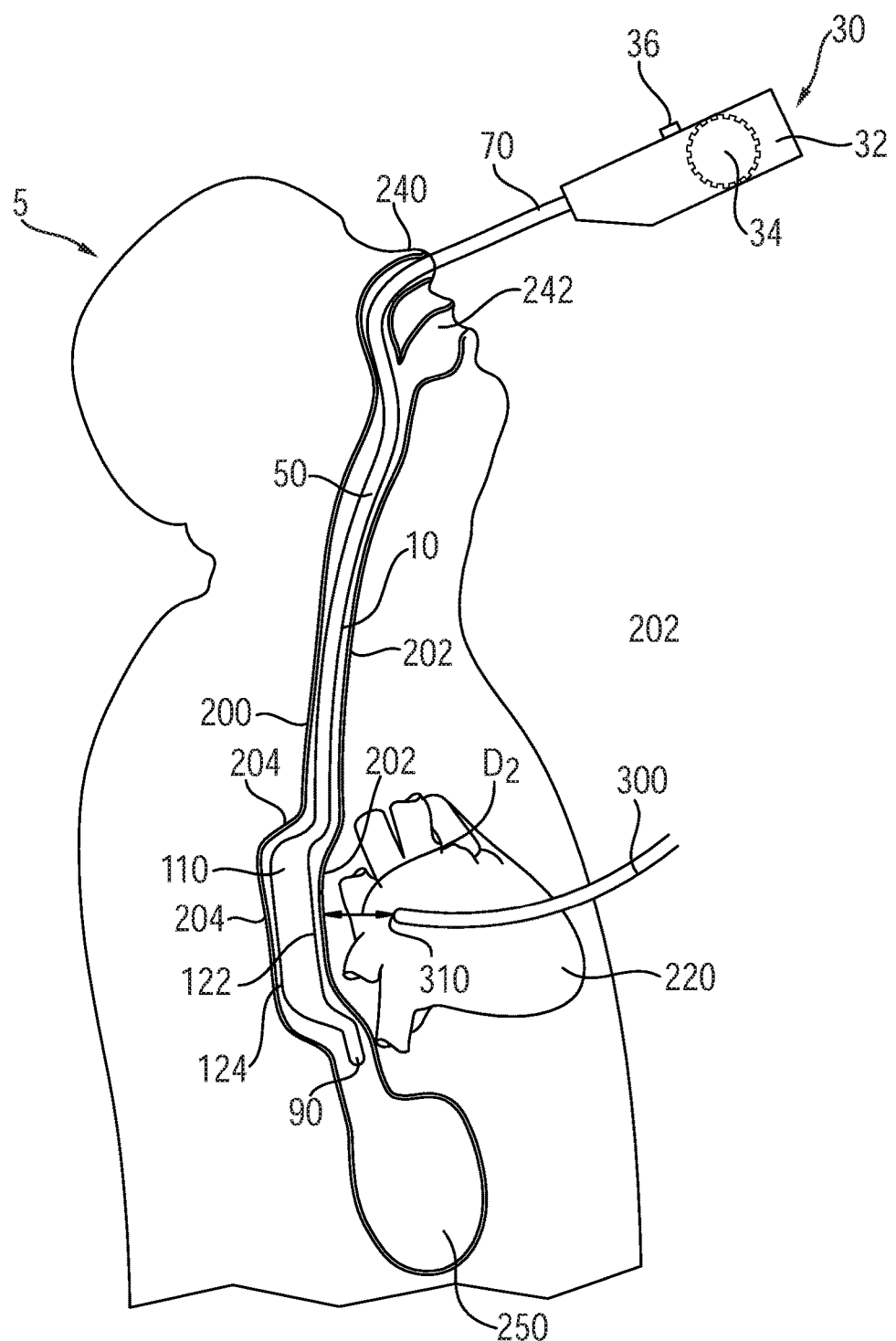
FIG. 3(b) shows a cross-sectional view of the esophageal displacement and repositioning catheter 10 of FIG. 3 positioned in esophagus 200 of patient 5, where catheter 10 is in an active, distended or deployed configuration.

FIG. 3(b) shows a cross-sectional view of the esophageal displacement and repositioning catheter 10 of FIG. 3(a) positioned in esophagus 200 of a patient 5, where catheter distendable section 110 of catheter 10 is in an active or distended position. As shown, trailing edge 204 of esophagus is now located a distance D2 away from ablation tip 310, esophagus 200 having been repositioned or displaced away from heart 220 by distendable section 110 of catheter 10. In some embodiments, catheter 10 and distendable section 110 are configured such that trailing edge 202 of esophagus 200 is located at least about 20 mm away from heart or ablation tip 310, at least about 25 mm away from heart or ablation tip 310, at least about 30 mm away from heart or ablation tip 310, at least about 35 mm away from heart or ablation tip 310, at least about 40 mm away from heart or ablation tip 310, at least about 45 mm away from heart or ablation tip 310, and/or at least about 50 mm away from heart or ablation tip 310. Catheter 10 may also be configured such that Distance D2 achievable by catheter 10 is adjustable or selectable according to a number of pre-selected or predetermined heights H1 and/or H2 that catheter 10 is configured to provide.

Figure 4:
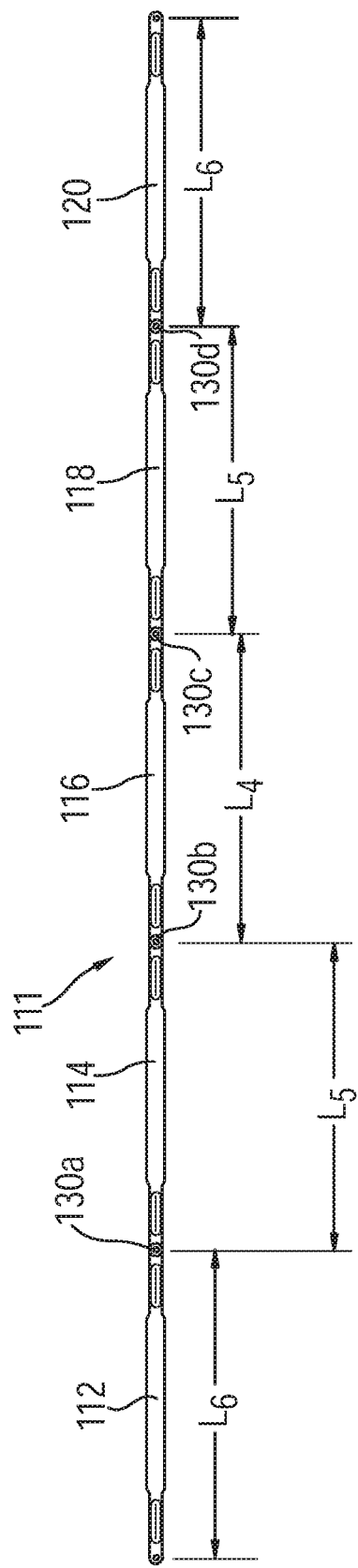
FIG. 4 shows a side view of one embodiment of a portion 111 of a distendable section 110 of an esophageal displacement and repositioning catheter 10.

Referring now to FIG. 4, there is shown a side view of one embodiment of a portion 111 of a distendable section 110 of an esophageal displacement and repositioning catheter, where a plurality of substantially rigid segments 112, 114, 116, 118 and 120 are configured to be located in or on distendable section 110 of catheter 10. As shown, and in on embodiment, segments 112, 114, 116, 118 and 120 are serially connected to one another by flexible or rotatable joints 130a, 130b, 130c, and 130d, and each of segments 112, 114, 116, 118 and 120 are rotatable through a prescribed range of angles (see, for example, FIGS. 6 and 7). Furthermore, in some embodiments segments 112, 114, 116, 118 and 120 can be configured to rotate within substantially a same plane such that torque can be efficiently transmitted from a proximal end of distendable section 110 to a distal end of distendable section 110. In some embodiments, segments 112, 114, 116, 118 and 120 are formed, machined or milled from a metal or a metal alloy, but may also be formed using suitably stiff plastics, polymers or other materials. In some embodiments, swivelable and rotatable joints 130a, 130b, 130c, and 130d with pins are constrained to move substantially within the same plane. Note that distendable section 110 may comprise fewer or more than the five sections 112, 114, 116, 118 and 120 shown in FIG. 4. For example, in some embodiments distendable section 110 comprises 3 such sections, 4 such sections, 6 such sections, 7 such sections, or any other suitable number of sections.

As shown in FIG. 4, and in one embodiment, distendable section comprises sections 112 and 120 having lengths L6, sections 114 and 118 having lengths L5, and central section 116 having length L4. As further explained and described below, lengths L4, L5 and L6 of sections 112-120, in combination with bending angles $\theta_1$, $\theta_2$, $\theta_3$, and $\theta_4$, angle range limiters 132a-132d, and constraining mechanisms 146 dimensions 146 (if employed) affect the particular dimensions L1, L2, L3, H1, and H2 obtained in a given design of catheter 10. By way of non-limiting example, in some embodiments, length L4 ranges between about 80 mm and about 230 mm, or between about 50 mm and about 150 mm, length L5 ranges between about 40 mm and about 140 mm, or between about 30 mm and about 100 mm, and length L6 ranges between about 80 mm and about 230 mm, or between about 40 mm and about 150 mm. Other lengths of, and ranges of lengths for, L4, L5 and L6 are also contemplated.

Figure 5:
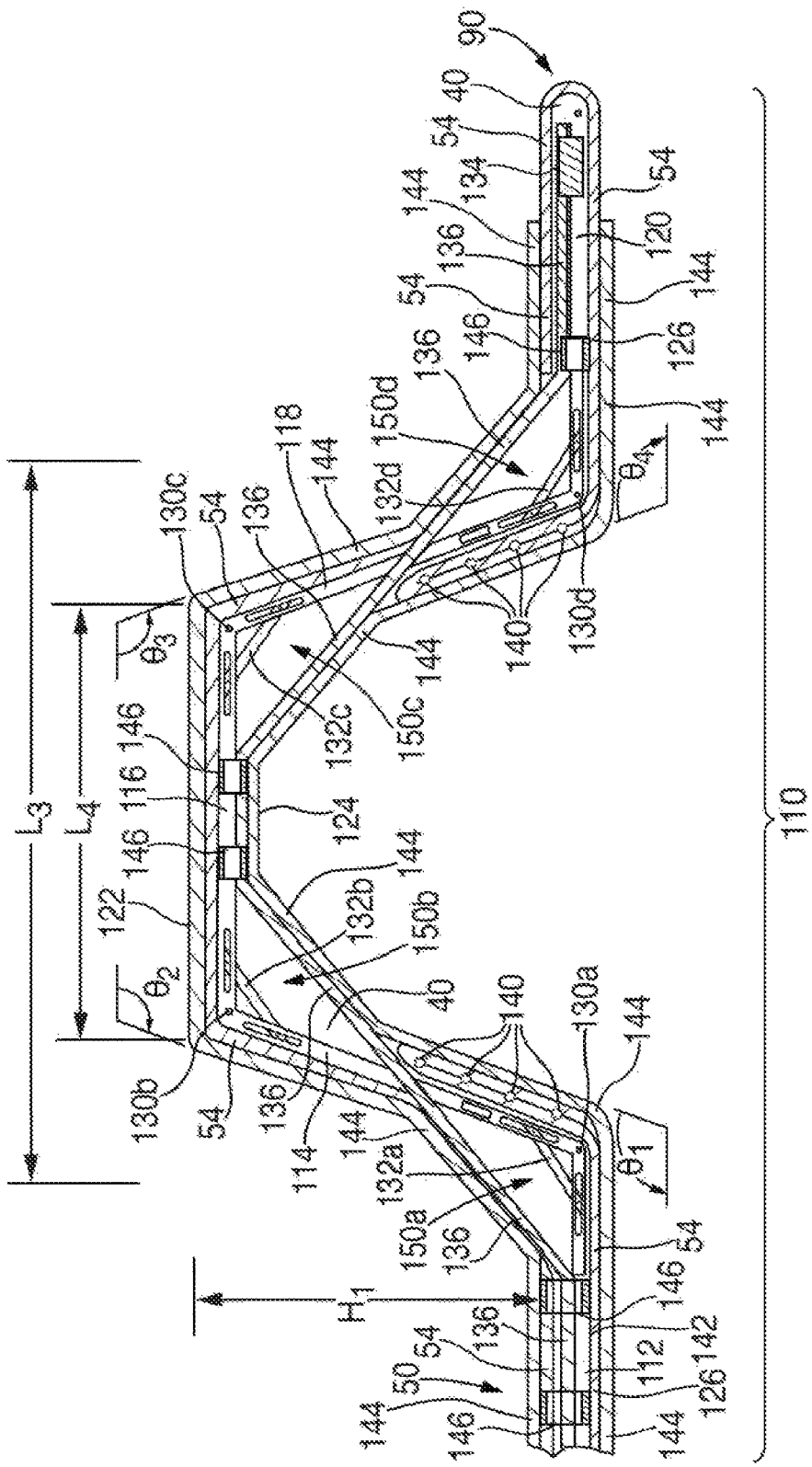
FIG. 5 shows a side cross-sectional view of one embodiment of a distendable section 110 of an esophageal displacement and repositioning catheter 10.
Figure 6:
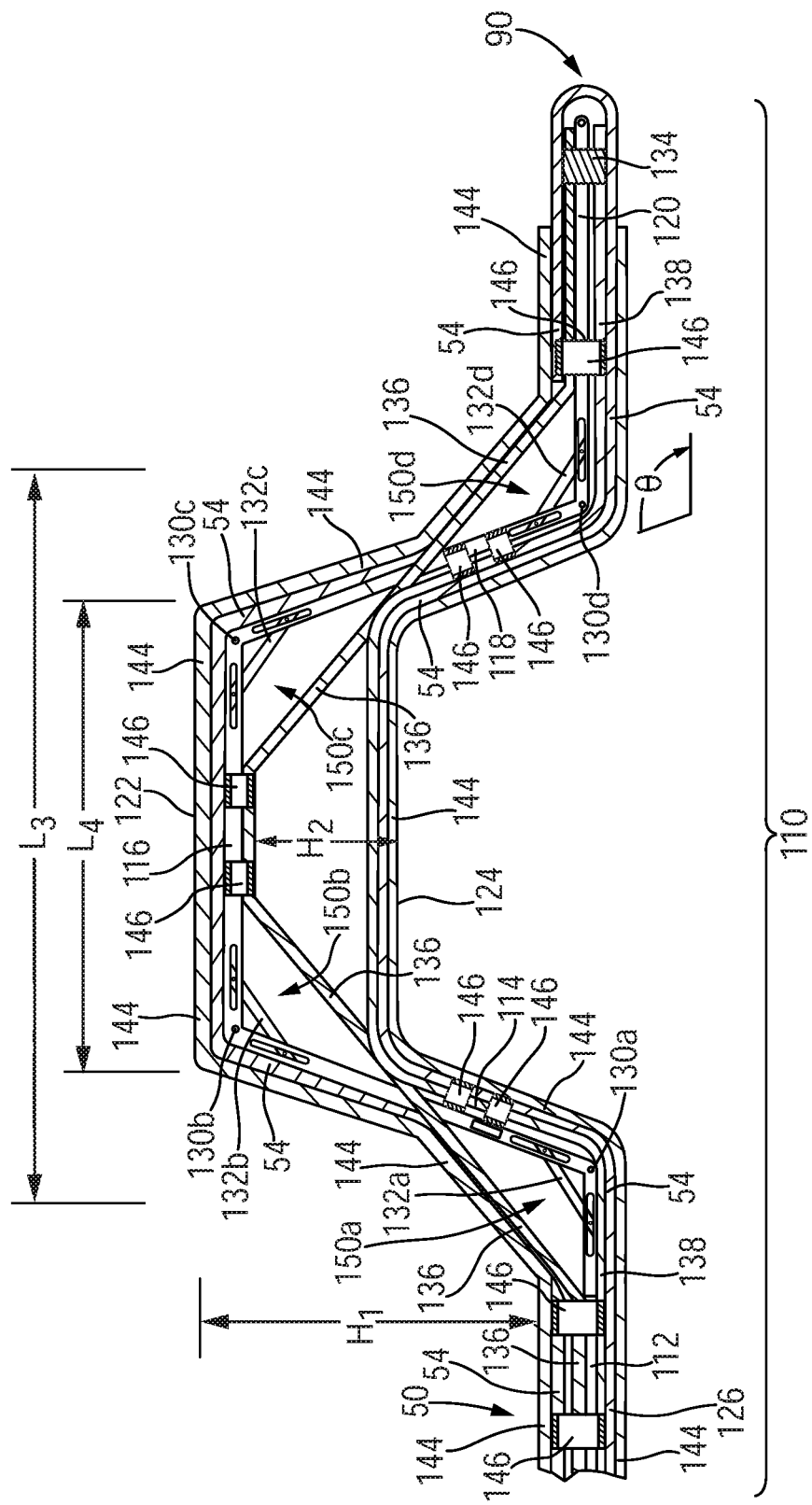
FIG. 6 shows a side cross-sectional view of another embodiment of a distendable section 110 of an esophageal displacement and repositioning catheter 10.

Not shown in FIG. 4, but shown in FIGS. 5 and 6, are range limiters 132a, 132b, 132c, and 132d corresponding to each rotational joint 130a, 130b, 130c, and 130d, respectively, which are configured to prevent the various individual sections of distendable section 110 from over-rotating with respect to one another and potentially causing the collapse of distendable section 110 in an undesired manner. Range limiters 132a through 132d may be configured in a number of different ways, including with wires formed of single, braided or stranded individual wires, strands of synthetic fibers such as KEVLAR™, telescoping members, rigid materials, stretchable or elastic materials or bands, or any other suitable material or structure. Range limiters 132a, 132b, 132c and 132d are configured to prevent over-rotation of joints 130a, 130b, 130c and 130d when first pulling member 136 is retracted in catheter 10 (or when second pulling member 138 is retracted in catheter 10, more about which is said below).

FIG. 5 shows a side cross-sectional view of one embodiment of distendable section 110 of esophageal displacement and repositioning catheter 10. Note that FIG. 5 shows various details of distendable section 110 not shown in the preceding Figures. Shown in FIG. 5 are elastic, flexible and/or stretchable member, sheath, covering, or outer layer 144, range limiters 132a, 132b, 132c, and 132d, ferrules, stand-offs or constraining mechanisms 146 through which first pulling member 136 slides or fits, first pulling member anchor 134, and substantially rigid sections 112, 114, 116, 118 and 120 disposed in a distended configuration having section bending angles $\theta_1$, $\theta_2$, $\theta_3$, and $\theta_4$ disposed therebetween. Note that in some embodiments bending angles $\theta_1$, $\theta_2$, $\theta_3$, and $\theta_4$ need not be the same, or that pairs of bending angles $\theta_1/\theta_4$ and/or $\theta_2/\theta_3$ need not be the same. Other configurations and combinations of bending angles $\theta_1$, $\theta_2$, $\theta_3$, and $\theta_4$ are also contemplated. In the illustrated embodiments, the bending angles may be limited by range limiters 132a, 132b, 132c and 132d, respectively. According to some embodiments, any one of angles $\theta_1$, $\theta_2$, $\theta_3$, and $\theta_4$ can range between about 90 degrees and about 160 degrees, between about 100 degrees and about 140 degrees, between about 105 degrees and about 135 degrees, and/or between about 110 degrees and about 130 degrees. Other angles and ranges of angles are also contemplated.

As shown In the embodiment of FIG. 5, distendable section 110 comprises a plurality of openings, slits, and/or recesses 150a, 150b, 150c, and 150d that are disposed or formed in the sidewalls 54 of catheter body 50 at or near the locations of joints 130a, 130b, 130c, and 130d, respectively, such that portions of first pulling member 136 can extend through such openings, slits or recesses and become located outside lumen 40 and catheter body 50 when first pulling member 136 is placed in the active or retracted position. Flexible member, sheath or covering 144 is configured to cover the openings, slits or recesses and the portions of first pulling member 136 extending outside lumen 40, and is further configured to become deformed and distended by such pulling member portions that are located outside catheter body 50 and lumen 40 when first pulling member 136 is in an active or retracted position. Ferrules or other suitable constraining mechanisms 146 hold and constrain first pulling member 136 while permitting slidable movement therethrough at suitable locations within distendable section 110 such that the amount or degree by which first pulling member 136 can extend outside catheter body 50 and lumen 40 is appropriately limited to correspond to the sizes or extent of openings 150a, 150b, 150c and 150d.

In one embodiment, outer layer 144 is configured to protect esophagus 200 from catheter 50 and pulling member 136, by "sucking" pulling member 136 back into lumen 40 of catheter 50 (or towards joints 130 or supports/range limiters 132). Outer layer 144 can also be configured to insulate or protect a patient's esophagus 200 or other portions of the patient's body from any metal, metal alloy or other materials incorporated into or forming a portion of catheter 50. In some embodiments, member, sheath, covering or outer layer 144 is formed of silicone or any other suitable flexible, elastic, and/or distendable, retractable and/or stretchable biocompatible material appropriate for use inside a patient's body, more about which is said below.

Further shown in FIG. 5 are temperature sensors 140, which according to one embodiment are incorporated into or attached to catheter 10, and which may also be incorporated into or attached to at least portions of distendable section 110 and member, sheath, covering, or outer layer 144 such that temperatures in the vicinity of distendable section 110 and/or other sections of catheter body 50 may be monitored during an AF ablation procedure. Such temperature sensors 140 may molded into covering, sheath or outer layer 144, or may be provided in any other suitable portion of catheter body 50; corresponding electrical conductors can be provided in catheter 10 to transmit temperature signals to handle 30 from sensors 140.

Alternatively, and as described in further detail below, temperature or others types of sensors (e.g., HIFU or high-intensity focused ultrasound sensors, navigation sensors, acoustic sensors, ultrasound sensors, radio-frequency coils or sensors, electrodes, off-the-shelf sensors or markers manufactured by third parties) may also be attached to the exterior or interior of catheter body 50 by clips, ferrules, bands or the like. Thus, temperature or other navigation or acoustic sensors, electrodes, transmitters or receivers may be provided external or internal to catheter body along and/or on the outer surface thereof, internal thereto, or in a coating or sheath disposed over catheter 50.

In those embodiments where temperature sensors 140 are employed, and for purposes of providing the most accurate temperature readings unaffected or substantially unaffected by the thermal properties of the materials from which catheter 50 or coatings or sheaths disposed thereover are formed, temperature sensors 140 may be disposed along catheter 50 such that they are positioned near or in close proximity to trailing edge 202 of esophagus 200, and therefore on an outside surface of catheter 50, when catheter 50 is employed to displace esophagus 200 away from ablation site 310. Temperature sensor signals may be transmitted wirelessly from catheter 50 to handle 30 or any other desired reception site (such as an external temperature signal monitoring and amplification device). Similarly, navigation and radio-opaque markers may be disposed along or in catheter body 50 and/or distendable section 110 to permit enhanced imaging of catheter 10 after it has been disposed within a patient 5 by fluoroscopic, computerized tomography (CT) scanning, or any other suitable imaging method.

FIG. 6 shows a side cross-sectional view of another embodiment of distendable section 110 of esophageal displacement and repositioning catheter 10, where second pulling member 138 is further included in catheter 10 and distendable section 110. As shown, second pulling member 138 is configured to be retracted after distendable section 110 has been deployed into a distended configuration by retracting first pulling member 136. Second pulling member 138 then causes elastic or distendable outer sheath or covering 144 to be drawn downwardly from section 116 in the direction of the trailing edge 204 of esophagus 200 (not shown in FIG. 6) such that trailing edge 124 of distendable section 110 located below section 116 may be positioned in closer proximity to trailing edge 204 of esophagus 200. Such positioning of trailing edge 124 of catheter 10 permits more accurate measurements of temperatures in the vicinity of the trailing edge 204 of esophagus 200 (when temperature sensors are provided in or near trailing edge 124, which are not shown in FIG. 6), and also permits at least portions of the trailing edge 204 of esophagus 200 to be drawn more closely to distendable section 110 when deployed inside the patient's esophagus, thereby reducing the risk of burn or injury to the esophagus during an AF ablation procedure.

In FIG. 6, distendable section 110 comprises a plurality of openings, slits, and/or recesses 150a, 150b, 150c, and 150d that are disposed or formed in the sidewalls 54 of catheter body 50 at or near the locations of joints 130a, 130b, 130c, and 130d, respectively, such that portions of first pulling member 136 and second pulling member 138 can extend through such openings, slits or recesses and become located outside lumen 40 and catheter body 50 when first pulling member 136 is placed in the active or retracted position, and when second pulling member is deployed into an active or retracted position. Flexible member, sheath or covering 144 is configured to cover the openings, slits or recesses 150a, 150b, 150c, and 150d, and the portions of first pulling member 136 extending outside lumen 40, and is further configured to become deformed and distended by such portions of first pulling member 136 that have become located outside catheter body 50 and lumen 40 when first pulling member 136 is in the active or retracted position. Ferrules or other suitable constraining mechanisms 146 hold and constrain first pulling member 136 and second pulling member 138 at suitable locations within distendable section 110 such that the amount or degree by which first pulling member 136 and second pulling member 138 can extend outside catheter body 50 and lumen 40 is appropriately limited to correspond to the sizes of openings 150a, 150b, 150c and 150d.

Continuing to refer to FIGS. 5 and 6, openings, recesses or slits 150a, 150b, 150c and 150d may possess different lengths and geometries along distendable section 110 and catheter body 50 according to the distention geometry of distendable section 110 that is desired to be achieved, as may the locations and types of constraining mechanisms 146 that are to be employed. In one embodiment, first pulling member 136 (and second pulling member 138, when employed), openings 150a through 150d, and constraining mechanisms 146 (if such mechanisms are utilized, which in some embodiments are not required as separate structural elements; see, e.g., FIGS. 7(a) and 8(a)) are together configured to permit a pulling member to be deployed outside opposing top and bottom surfaces of catheter body 50 and distendable section 110, such as the top and bottom surfaces of catheter body 50 shown in FIGS. 5 and 6.

The combination of substantially rigid sections 112 through 120, interconnecting joints 130a through 130d, openings 150a through 150d, range limiters 132a through 132d (if employed as separate structural elements), pulling members 136 and/or 138, and distendable cover or sheath 144 together result in a distendable section 110 that can be controllably and safely deployed to move a patient's esophagus 200 a safe distance D2 away from the patient's heart 220.

The respective specific lengths of sections 112-120 and openings 150a-150d, and the specific locations of constraining mechanisms 146 (if employed, as noted above) can all be varied and customized so that distendable section 110 and dimensions corresponding H1, H2, L3, L4 are capable of assuming an appropriate distended configuration that is suitable for a given type of esophageal displacement procedure, for a given patient's needs, and/or for a given patient's individual anatomical geometry. Thus, for an infant or child a small and compact distendable section 110 with certain appropriate dimensions H1, H2, L3, L4 may be employed, while for a large tall male patient a relatively large distendable section 110 and certain other appropriate dimensions may be employed. The length and amount of distension of the esophagus provided by distendable section 110 can also be adjusted by selecting dimensions H1, H2, L3, and/or L4 to provide the desired or optimal length and amount of distention of the esophagus for a given patient, class or type of patient, and/or type of medical or surgical procedure or treatment that is to be carried out on a patient and/or class or type of patient.

Referring now to FIGS. 5 and 6 as two reference points, in other embodiments distendable section 110 comprises a segmented catheter body 50, where individual segments of catheter body 50 are disposed individually over corresponding jointed portions of sections 112, 114, 116, 118 and 120, and where such individual segments of catheter body 50 are separated from one another by intervening portions between them having no or attenuated portions of a catheter body 50 disposed thereover, but where, for example, outer layer 144 is disposed between such individual segments of catheter body 50. In such embodiments, no openings, recesses, slots or slits are necessarily required through which pulling members 136 and/or 138 can extend, as no intervening portions of catheter body 50 are disposed over the portions of pull wires 136 and/or 138 which are configured to extend outwardly away from sections 112, 114, 116, 118 and/or 120 when distendable section 110 is in an active or deployed configuration.

In some embodiments, portions of substantially rigid sections 112, 114, 116, 118 and 120, and especially those portions of substantially rigid sections 112, 114, 116, 118 and 120 located at or near joints 130a-130d, are configured to be rounded and smooth so that the portions of at least one outer layer 144 disposed near joints 130a-130d are not ripped, torn or damaged as outer layer 144 is stretched over joints 130a-130d when distendable section 110 is placed in a deployed or active configuration.

After having read and understood the specification and drawings hereof, those skilled in the art will now understand that numerous permutations, adaptations, modifications, and combinations of the various structural elements disclosed and described herein are possible that can result in a distendable section 110 comprising one or more pull wires or pull members that are configured to extend outwardly away from any one or more of sections 112, 114, 116, 118 and 120, and thereby permit distendable section 110 to assume a distended or active deployed configuration, without departing from the scope and spirit of the inventions shown herein.

Figure 7A:
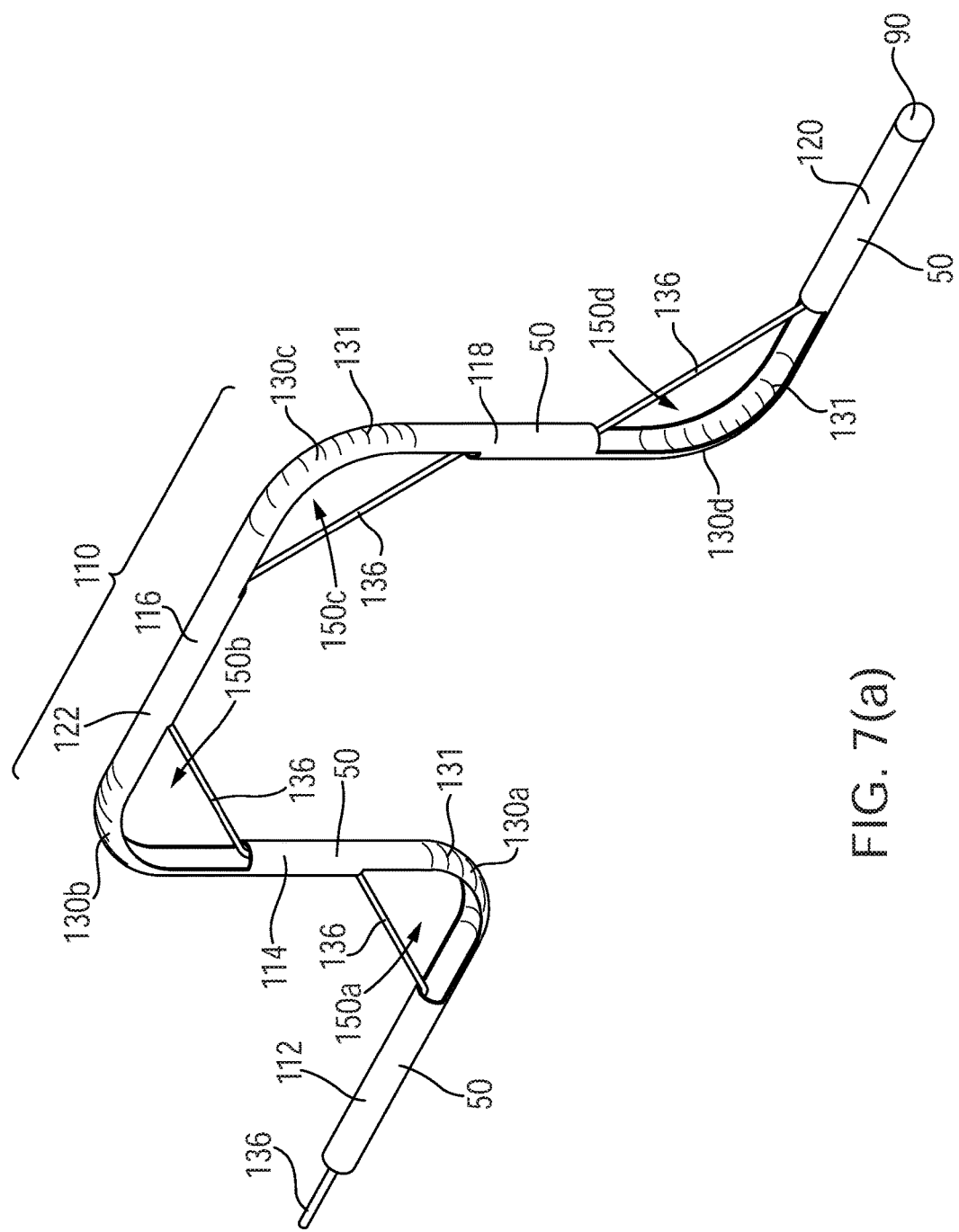
FIG. 7(a) shows a top perspective view of yet another embodiment of a distendable section 110 of an esophageal displacement and repositioning catheter 10.
Figure 7B:
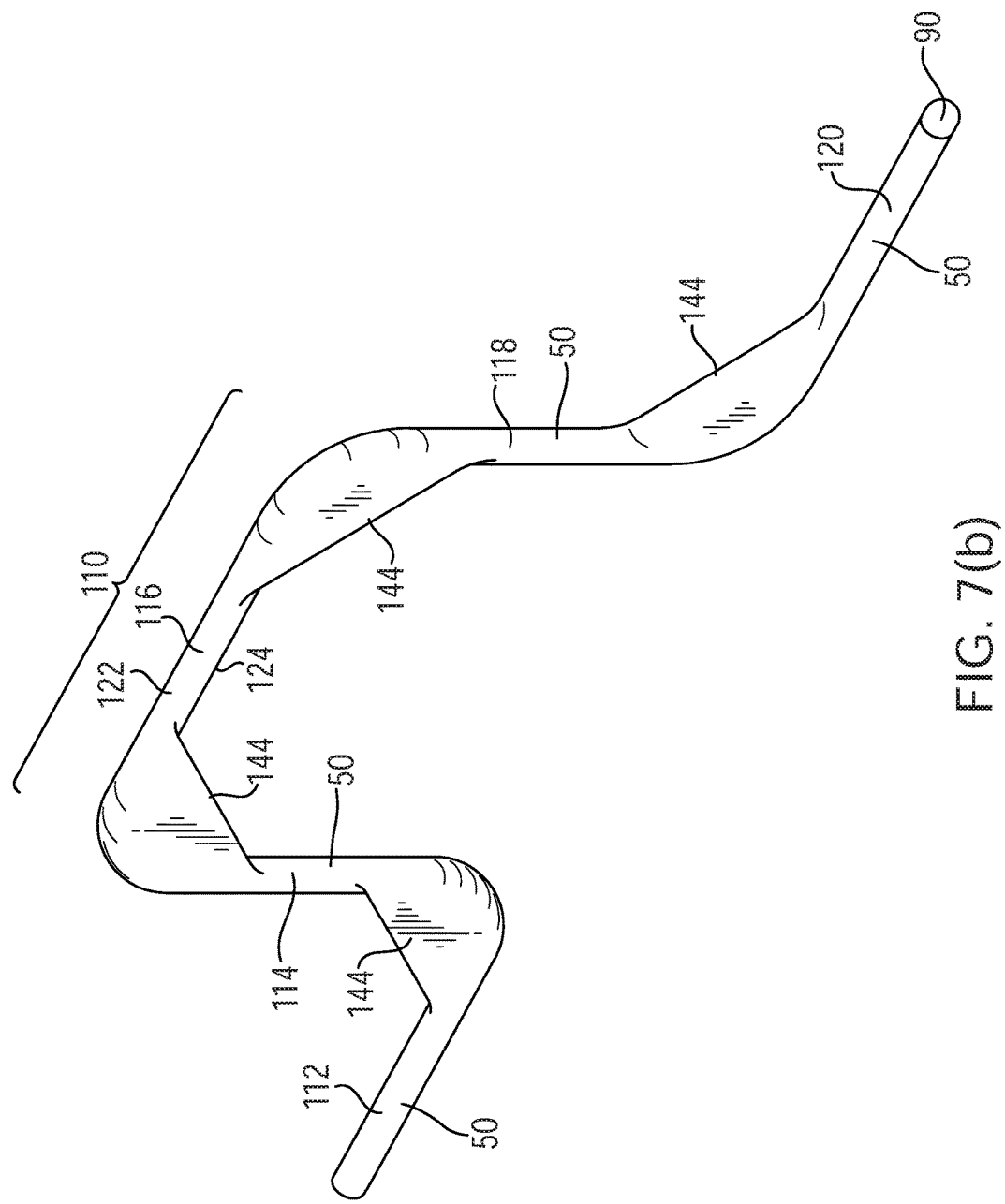
FIG. 7(b) shows distendable section 110 of esophageal displacement and repositioning catheter 10 of FIG. 8(a) having an elastic, flexible or distendable sheath 144 positioned thereover.
Figure 8A:
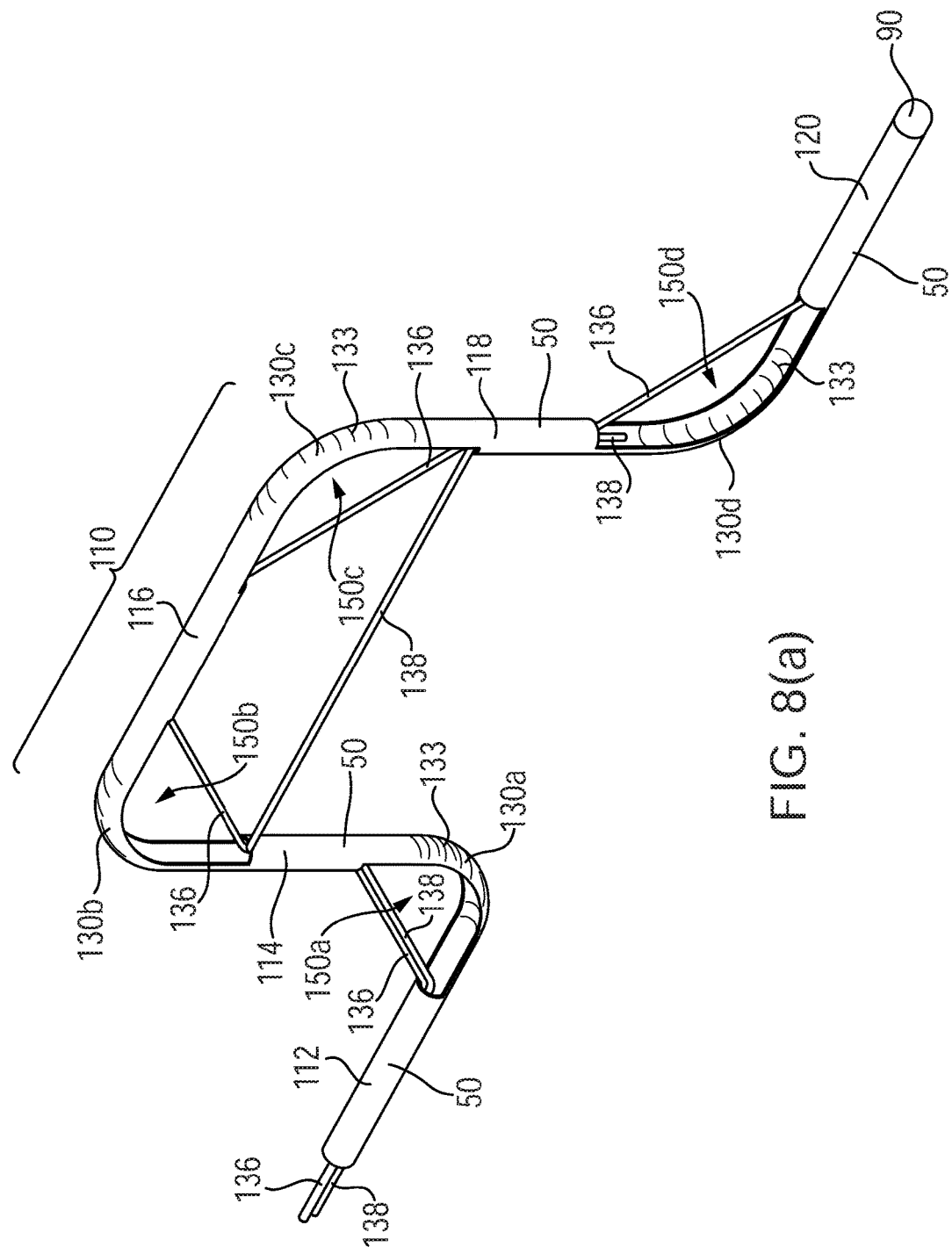
FIG. 8(a) shows a top perspective view of still another embodiment of a distendable section 110 of an esophageal displacement and repositioning catheter 10.

FIG. 7(a) shows a top perspective view of yet another embodiment of a distendable section 110 of an esophageal displacement and repositioning catheter 10. In FIG. 7(a), and for purposes of easing illustration and description, outer elastic, distendable, stretchable and/or flexible member, layer, sheath or covering 144 is not shown (but is shown in FIG. 7(b)). In addition, and again for purposes of easing illustration and description, range limiters 130a, 130b, 130c and 130d are not shown in FIG. 7(a) (but are shown in FIG. 8(c)). In FIG. 7(a), distendable section 110 comprises a series of sections 112, 114, 116, 118 and 120 that are joined by flexible joints 130a, 130b, 130c and 130d. In one embodiment, sections 112, 114, 116, 118 and 120, and flexible joints 130a, 130b, 130c and 130d, are all formed of thin-walled stainless steel or any other suitable metal, metal alloy, plastic or polymer. Flexible joints 130a through 130d can be formed by suitably slitting or cutting distendable section 110 at appropriate locations 131 corresponding to the locations of flexible joints 130a, 130b, 130c and 130d, thereby to form such bendable joints. Joints 130a, 130b, 130c and 130d each also comprises a plurality of openings, slits or recesses 150a, 150b, 150c and 150d cut or formed into distendable section 110, where such openings, slits or recesses are disposed at suitable locations along distendable section 110.

Note that in addition to first and/or second pulling members 136 and/or 138 extending all the way through continuous openings 150*a*, 150*b*, 150*c* and 150*d* and outwardly away from catheter body 50 near the locations of joints 130*a*, 130*b*, 130*c* and 130*d* as shown in FIG. 7(*a*), in other embodiments openings 150*a*-150*d* can also comprise discrete non-continuous first and second holes 150 corresponding to each joint 130, where, for example, first and/or second pulling members 136 and/or 138 are routed from inside catheter 50 proximally through the first hole 150 located in a first position before a given joint, to outside the catheter body 50 over or near the joint 130, and then back inside catheter body 50 distally at the second hole 150 located in a second position after the given joint. Joint 130 can then be manipulated into a deployed position by retracting the pulling member 136 and/or 138, where the pulling member extends away from and outside catheter body 50 between the first and second holes 150. Similar configurations of holes 150 and pulling members 136/138 may be employed in other joints 130. In such embodiments where pulling member 136 and/or 138 is routed outside catheter body 50 between holes 150, outer layer or covering 144 is positioned over and covers those portions of pulling members 136 and/or 138 that are disposed outside catheter body 50 between holes 150. Thus, it will now be seen that holes, recesses, openings, slits and recesses 150 can be configured in many different combinations, permutations and embodiments that permit a pulling member to extend outside catheter body 50, and that permit the necessary amount of bending of joints 130 to be provided so as to permit a suitable amount of distention of a patient 5's esophagus 200.

Slits or cuts 131 have suitable dimensions of width and length to permit a desired amount, degree and type of bending at joints 130*a*, 130*b*, 130*c* and 130*d*. Openings, recesses or slits 150*a*, 150*b*, 150*c* and 150*d* have dimensions appropriate to permit portions of first pulling member 136 to extend through such openings, slits or recesses and become located outside lumen 40 and catheter body 50 when first pulling member 136 is placed in the active or retracted position.

As shown in FIG. 7(*b*), flexible member, layer, sheath or covering 144 is configured to cover openings, slits or recesses 150*a* through 150*d* and the portions of first pulling member 136 that extend outside lumen 40, and is further configured to become deformed and distended by such portions of first pulling member 136 that have become located outside catheter body 50 and lumen 40 when first pulling member 136 is in the active or retracted position. In the embodiment shown in FIG. 7(*a*), openings, recesses or slits 150*a*, 150*b*, 150*c* and 150*d* are configured to hold and constrain first pulling member 136 at suitable locations within distendable section 110 such that the amount or degree by which first pulling member 136 can extend outside catheter body 50 and lumen 40 is appropriately limited to correspond to the sizes of openings 150*a*, 150*b*, 150*c* and 150*d*.

In some embodiments of distendable section 110 shown in FIGS. 7(*a*) and 7(*b*), the thickness of sidewalls 54 of catheter 50 can range between about 0.2 mm and about 0.8 mm, and catheter 50 has an overall diameter ranging between about 4 mm and about 10 mm. Diameters of about 6 mm and less for catheter 50 are preferred, as they can more easily be inserted in esophagus 200 through patient's nose 240 (instead of through patient's mouth 242).

Figure 8B:
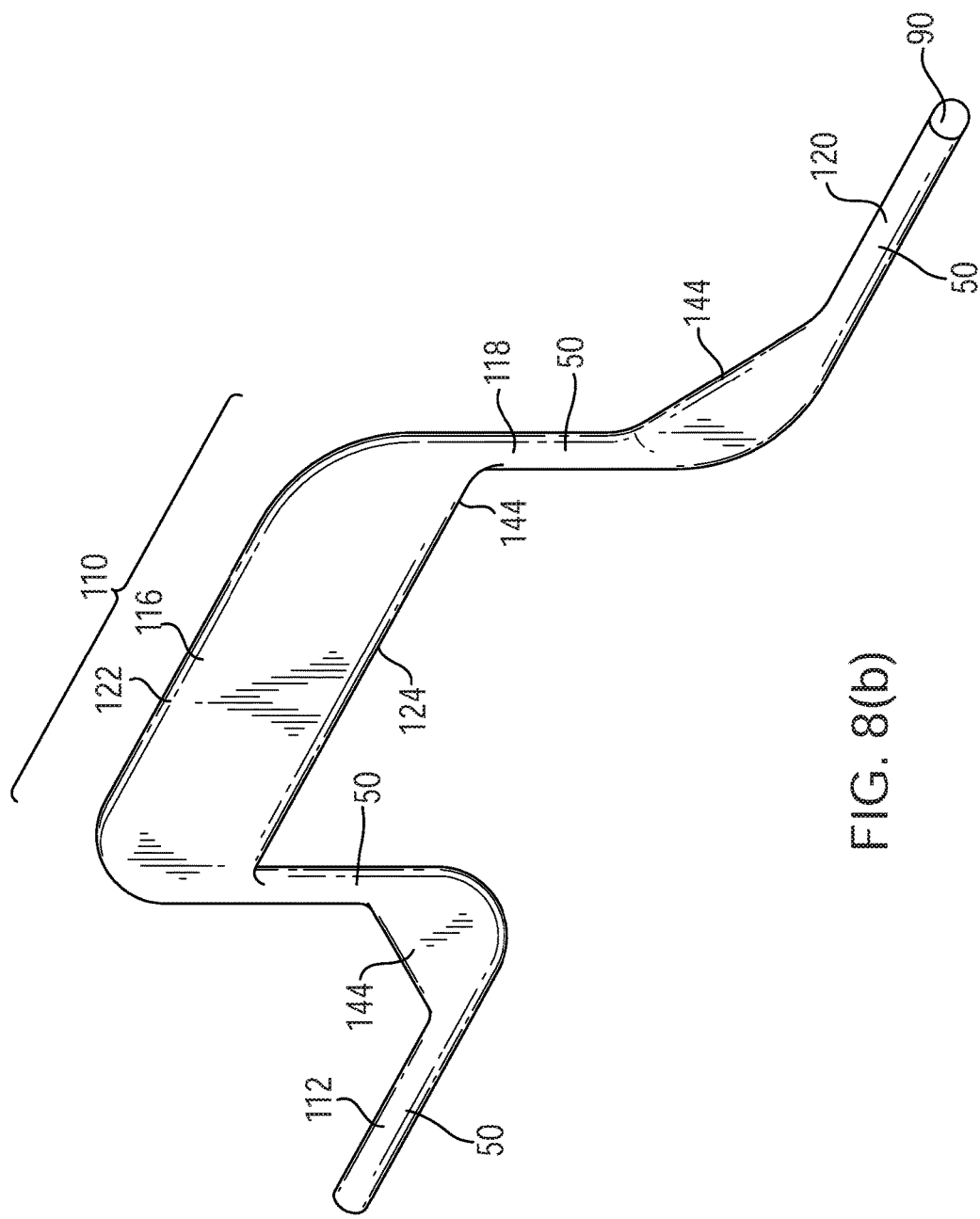
FIG. 8(b) shows distendable section 110 of esophageal displacement and repositioning catheter 10 of FIG. 8(a) having an elastic, flexible or distendable sheath 144 positioned thereover.
Figure 8C:
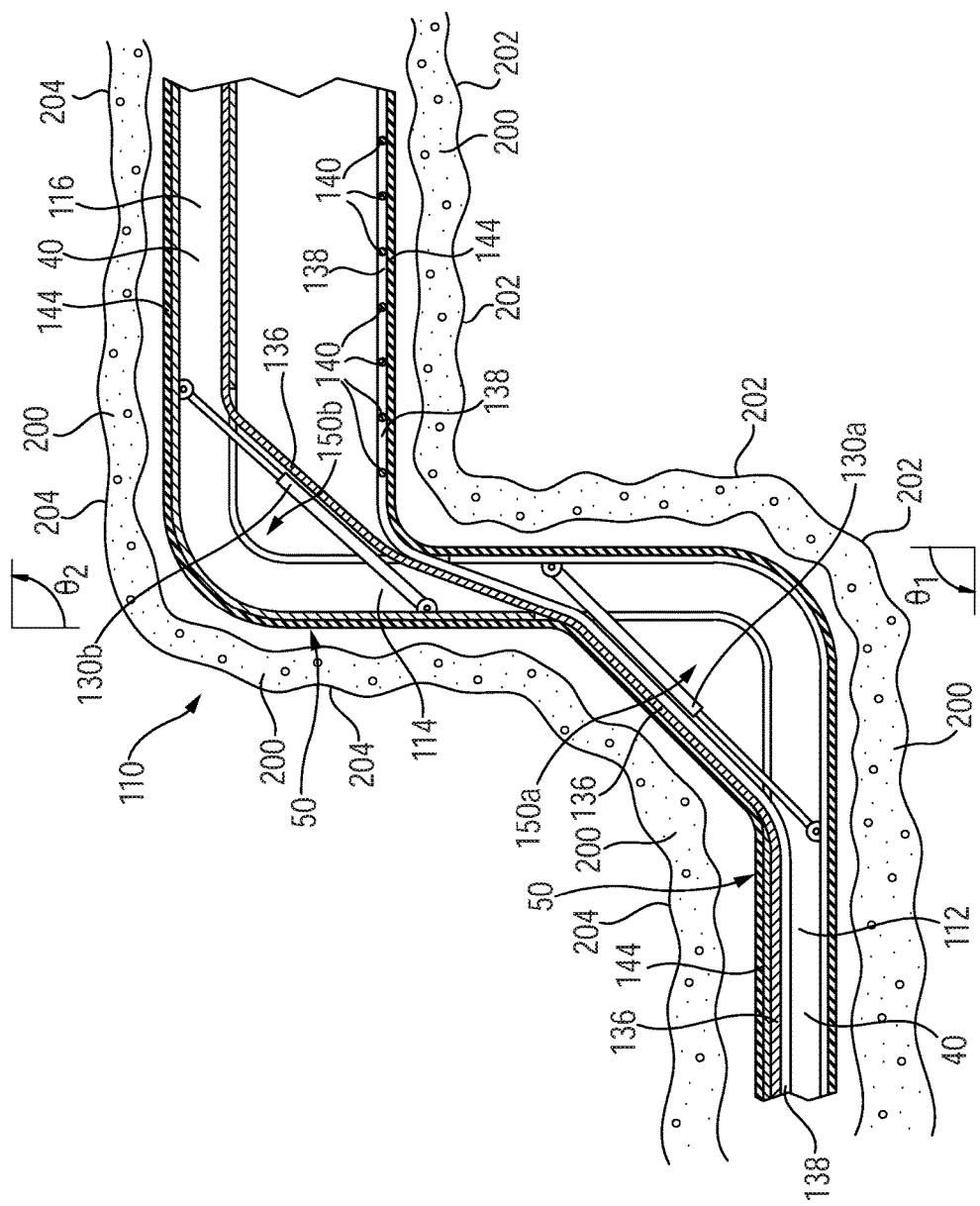
FIG. 8(c) shows a cross-sectional view of a portion of another embodiment of a distendable section of an esophageal displacement and repositioning catheter.

Referring now to FIG. 8(*a*), first pulling member 136 is configured to cause distendable section 110 to assume a distended configuration when retracted through the action of a user or health care provider, and exits distendable section 110 through openings, recesses or slits at locations 150*a*, 150*b*, 150*c*, and 150*d* formed in the sidewalls of distendable section 110 opposite flexible joints 130*a*, 130*b*, 130*c* and 130*d*. Second pulling member 138 is configured to cause trailing edge 124 of outer sheath 144 to be pulled downwardly away from section 116 when retracted through the action of a user or health care provider in a fashion similar to that described above with respect to FIG. 6.

FIG. 8(*b*) shows distendable section 110 of FIG. 8(*a*) in a distended configuration, but with flexible, elastic or distendable member, sheath, covering or layer 144 disposed over the outer surfaces thereof. As shown in FIG. 8(*b*) and in other Figures, member, sheath, covering and/or layer 144 expands or stretches outwardly when distendable section 110 and pulling members 136 and 138 are together configured in an active or distended position, and retracts or pulls inwardly when distendable section 110 and pulling members 136 and 138 are together configured in an inactive or retracted position.

As noted above, in some embodiments member, sheath, covering or outer layer 144 is formed of silicone or any other suitable flexible, elastic, and/or distendable, retractable and/or stretchable biocompatible material appropriate for use inside a patient's body. Such materials for sheath or cover 144 include, but are not limited to, flexible, stretchable, distendable and retractable meshes, flexible, stretchable, distendable and retractable silicone-based materials, medical-grade silicone, rubber silicone materials, latex-based materials, latex, rubber-based materials, rubber, rubber latex materials, urethane-based materials, polyurethane-containing materials, suitably flexible polyethylene-containing materials, polyethylene terephthalate (PET)-containing materials, polyisoprene-containing materials, polypropylene, fluoroplastic, polymers, elastomers, and thermoplastic elastomers, and combinations and mixtures of the foregoing. Other materials that are biocompatible, flexible, stretchable, and retractable, and that are otherwise safe for use inside the human body, are also contemplated. In some embodiments, member, sheath, covering or outer layer 144 has a flexural modulus ranging between about 90 MPa and about 500 MPa.

FIG. 8(*c*) shows a cross-section of a portion of another embodiment of distendable section 110, where telescoping range limiters also act as joints 130*a* and 130*b*, and are attached to sidewalls 54 of catheter body 50. Other types of range limiters and joints are also contemplated, as will become apparent to one of skill in the art after having read and understood the present specification and drawings. As shown in FIG. 8(*c*), the edges of openings 150*a* and 150*b* guide and restrict the movement of wires 136 and 138 inside lumen 40. Temperature or other sensors or markers 140 may be disposed along trailing edge 124, for example to measure esophageal temperature during an AF ablation procedure or permit accurate imaging of the position of catheter 10 in patient 5.

FIGS. 9(*a*) through 9(*e*) illustrate certain features according to one embodiment of catheter 10. The various dimensions shown in FIGS. 9(*a*) through 9(*e*) are merely illustrative, and are not intended to be limiting. Those skilled in the art, upon having read and understood the present disclosure will understand and appreciate that other dimensions may be employed without departing from the scope and spirit of the inventions described and disclosed herein.

Figure 9A:
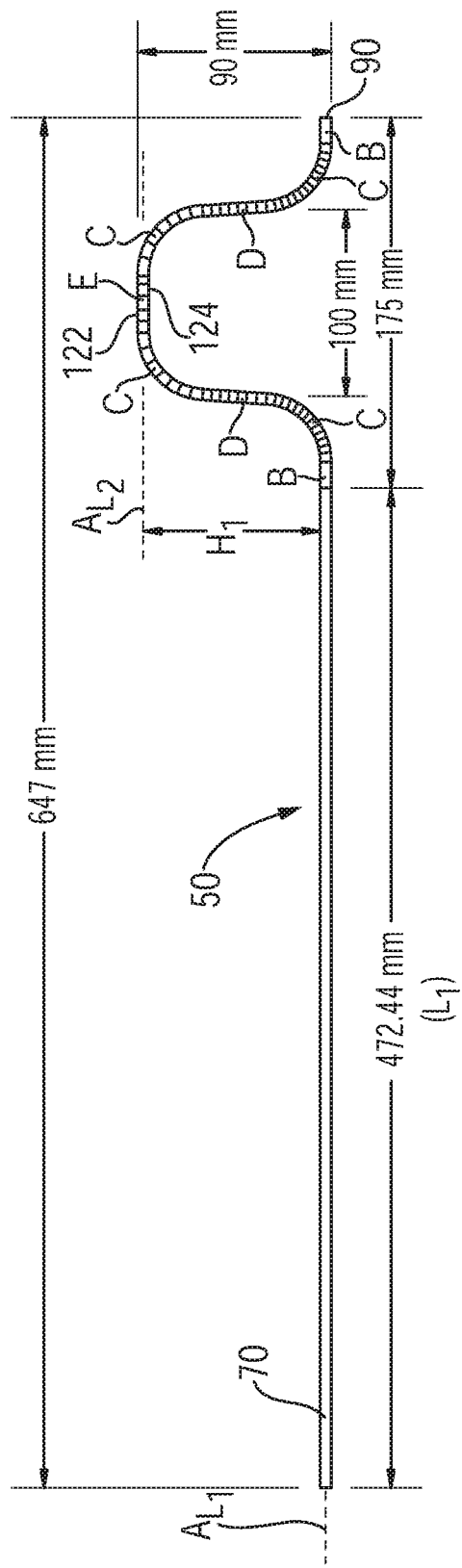
FIG. 9(a) shows a side view of still another embodiment of catheter body 50, proximal end 70, distal end 90 and distendable section 110 of an esophageal displacement and repositioning catheter 10.

FIG. 9(a) shows a side view of another embodiment of catheter body 50, proximal end 70, distal end 90 and distendable section 110 of an esophageal displacement and repositioning catheter 10. For purposes of easing illustration, note that FIG. 9(a) does not show catheter handle 30 (which would be included in any complete catheter 10). Also note that for purposes of easing illustration slots 131 are not shown on all portions of catheter 50 in FIG. 9(a), and that none of slots 131 shown in FIGS. 10(a) through 10(e) extend around the entire circumference of catheter body 50. Openings, recesses and/or slits or slots 150a through 150d are also not shown explicitly in FIGS. 9(a) through 9(e).

Figure 9B:
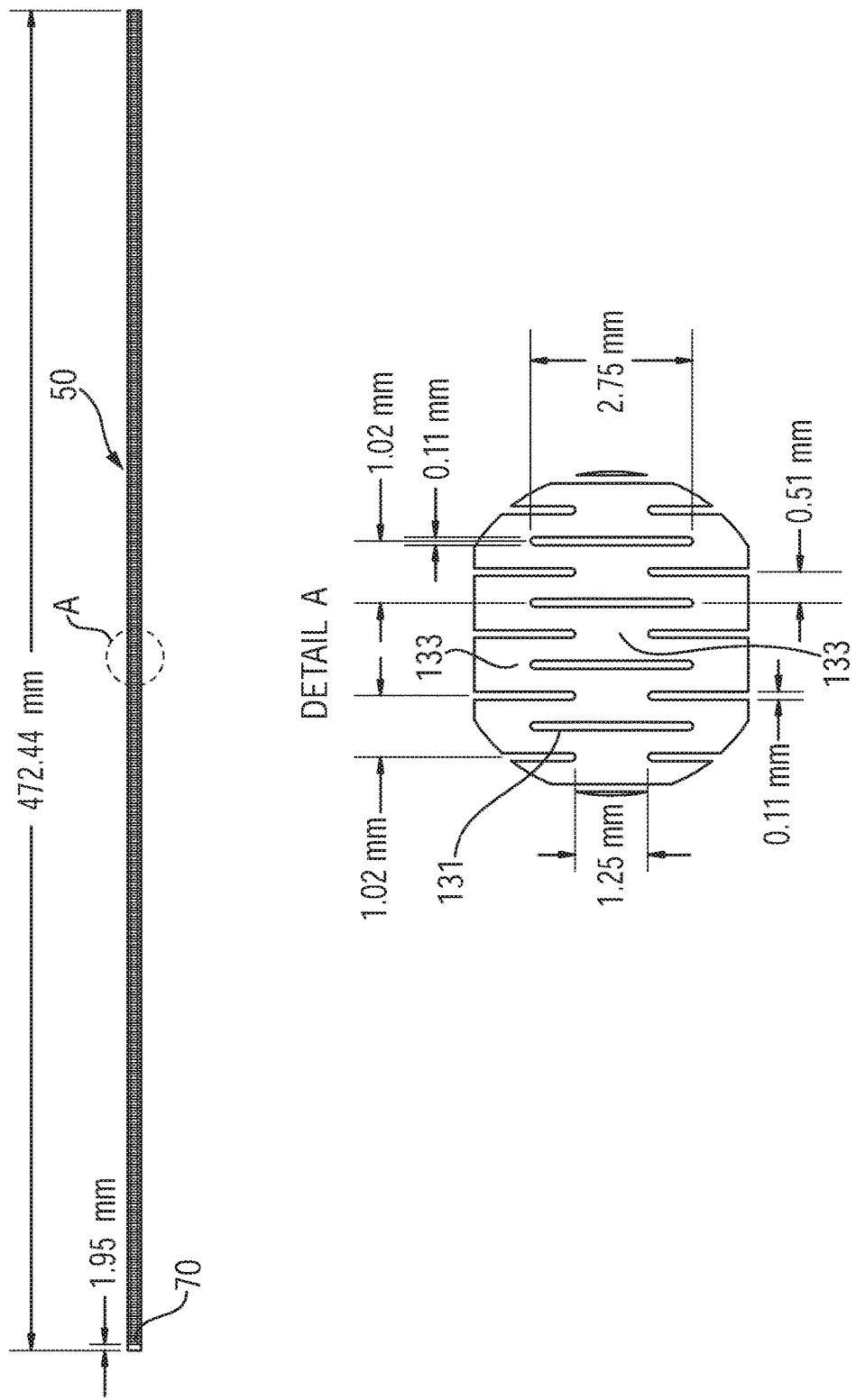
FIG. 9(b) shows a side view of catheter body 50 of esophageal displacement and repositioning catheter 10 shown in FIG. 9(a), including detail A thereof.

FIG. 9(b) shows a side view of catheter body 50 of esophageal displacement and repositioning catheter 10 shown in FIG. 9(a), including detail A thereof. As shown, slits or slots 131 are cut or formed along catheter body 50, thereby imparting bendability to catheter body 10, which permits catheter body 10 to be inserted through patient's nose 240 or mouth 242, and then into patient's esophagus 200. Detail A in FIG. 9(b) shows that slits or slots 131 are cut or otherwise formed in catheter body 50 such that each slit or slot does not circumscribe the entire circumference of catheter body 50, and instead is formed or cut only through a prescribed range of the circumference; a matrix 133 of uncut material thus extends around and between slots or slits 131. Such a slot or slit configuration imparts a substantial degree of torsional rigidity to catheter 10 such that a rotation of proximal end 70 of catheter body 50 through a given number of degrees results in the same or substantially the same number of degrees of rotation at distal end 90 of catheter body 50. In some embodiments, and depending on the number, spacing, depth, width and length of the various slits or slots disposed along catheter body 50, a 1:1 ratio or essentially a 1:1 turn ratio can be provided between the proximal and distal ends 70 and 90 of catheter 50 as proximal end 70 of catheter 10 is rotated by a user in the patient's esophagus such that a health care provider can place distendable section 110 in an optimal position with respect to ablation site 310 (e.g., such that distendable section 110 bows or deflects outwardly and away from ablation site 310). Such positioning may be effected with the aid of fluoroscopy or other well-known medical imaging methods. According to some embodiments, the torsional rigidity of catheter 10 is provided by matrix 133 of solid and uncut or unslotted metal, metal alloy or similarly rigid material that extends between proximal and distal ends 70 and 90 of catheter body 10, where the matrix extends between and around slots or slits 131.

Detail A in FIG. 9(b) shows such a configuration of slots or slits, where merely by way of non-limiting illustrative example slots or slits 131 are spaced 1.02 mm apart in the longitudinal direction, and 1.25 mm apart in the axial direction, where slots or slits 131 are 0.11 mm wide, and matrix 133 extends and is disposed between such slots or slits 131. Those skilled in the art, upon having read and understood the present disclosure, will appreciate that numerous other configurations, dimensions, spacings and other characteristics of slots or slits 131 and matrix 133 may be employed to impart both bendability and torsional rigidity to catheter body 50. For example, slots or slits 131 may be spaced apart in the longitudinal direction from one another between about 0.5 mm and about 1.5 mm, may be spaced apart in the axial direction between about 0.75 mm and about 1.75 mm, and may be between about 0.05 mm and about 0.2 mm wide. Other spacings and widths are also contemplated.

Figure 9C:
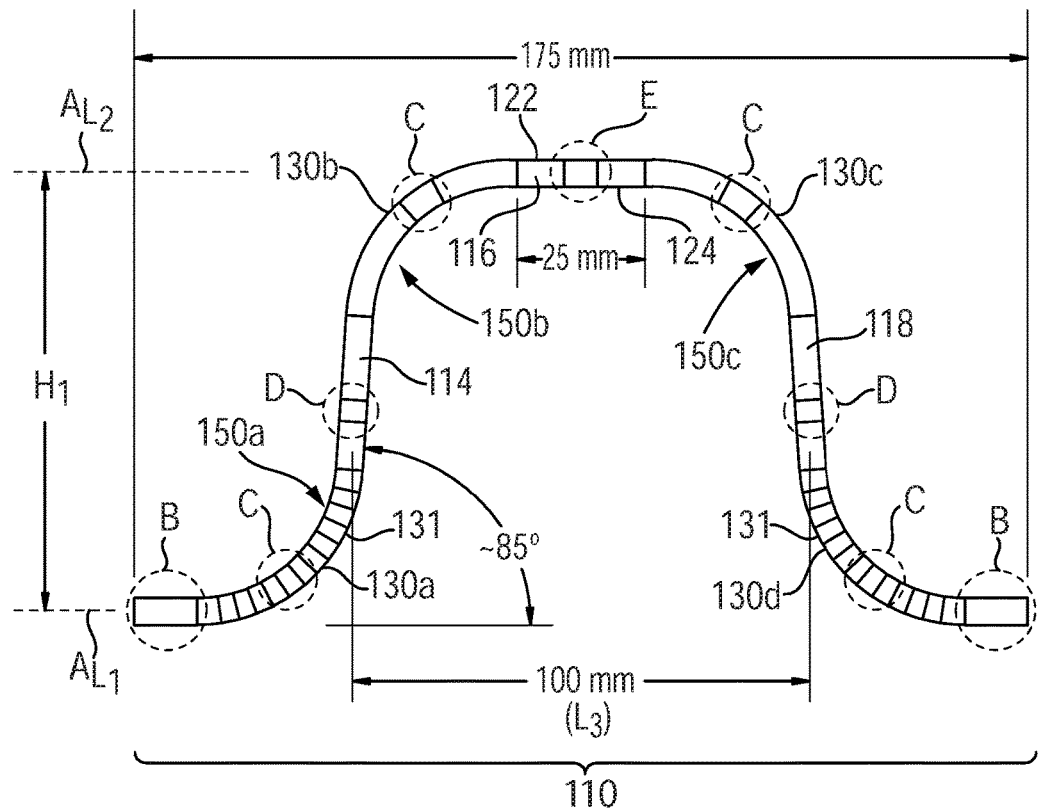
FIG. 9(c) shows a side view of distendable section 110 of esophageal displacement and repositioning catheter 10 shown in FIG. 9(a)
Figure 9D:
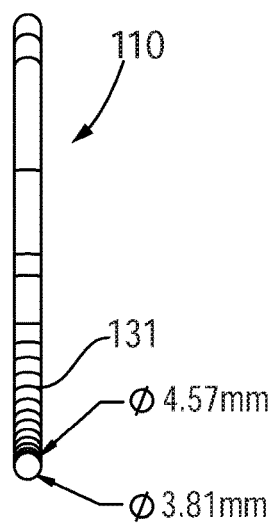
FIG. 9(d) shows an end view of distendable section 110 of esophageal displacement and repositioning catheter 10 shown in FIG. 9(c)

FIG. 9(c) shows a side view of distendable section 110 of esophageal displacement and repositioning catheter 10 shown in FIG. 9(a). FIG. 9(d) shows an end view of distendable section 110 of esophageal displacement and repositioning catheter 10 shown in FIG. 9(c). Details B, C, D and E are shown enlarged in FIG. 9(e). The various dimensions shown in FIGS. 10(a) through 10(e) are merely illustrative, and are intended to show only a few of many different embodiments.

Figure 10A:
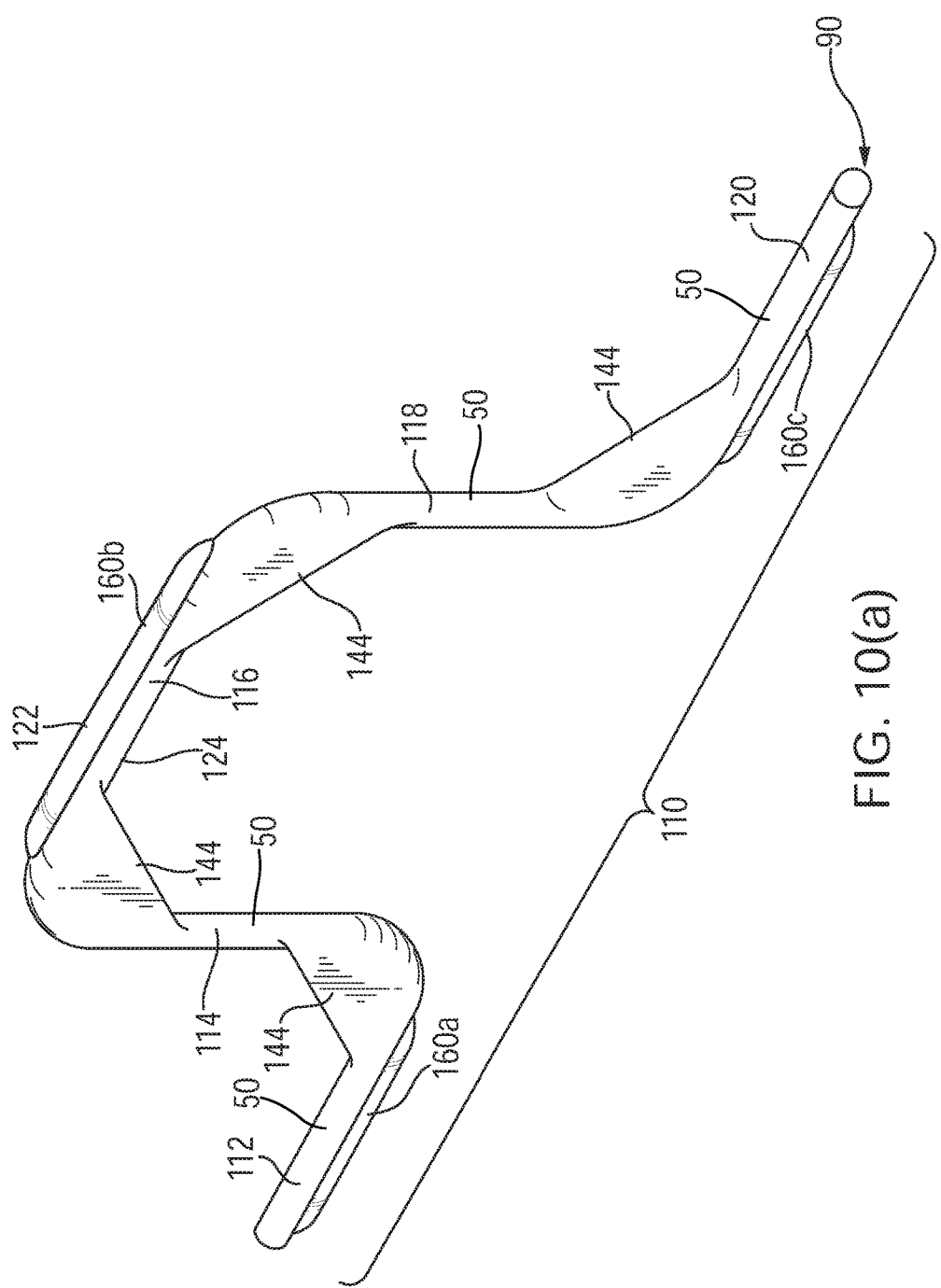
FIG. 10(a) shows a top perspective view of still another embodiment of a distendable section 110 of an esophageal displacement and repositioning catheter 10 comprising balloons 160a, 160b and 160c in non-deployed or non-inflated states.
Figure 10B:
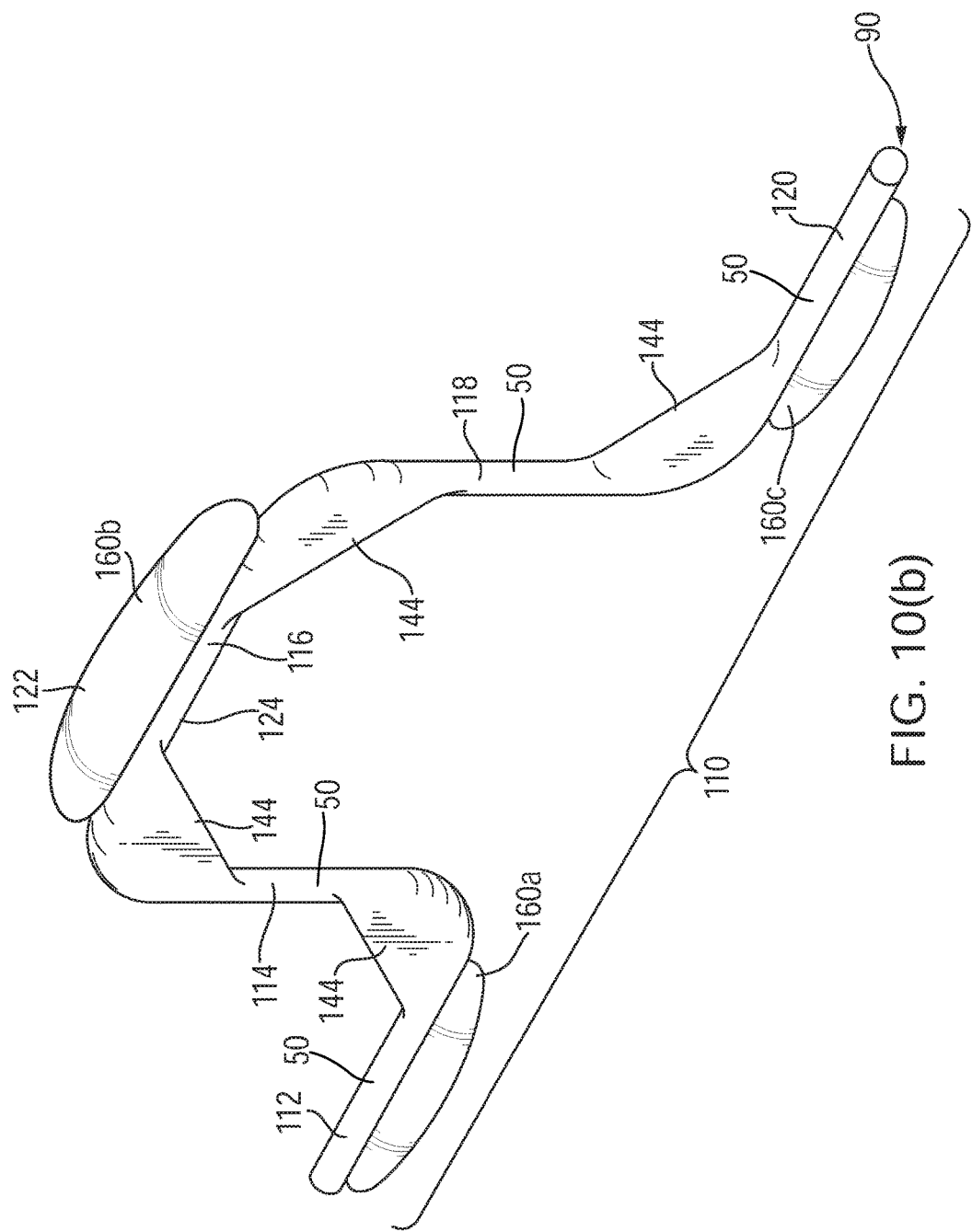
FIG. 10(b) shows distendable section 110 of esophageal displacement and repositioning catheter 10 of FIG. 10(a) with balloons 160a, 160b and 160c in deployed or inflated states.
Figure 10C:
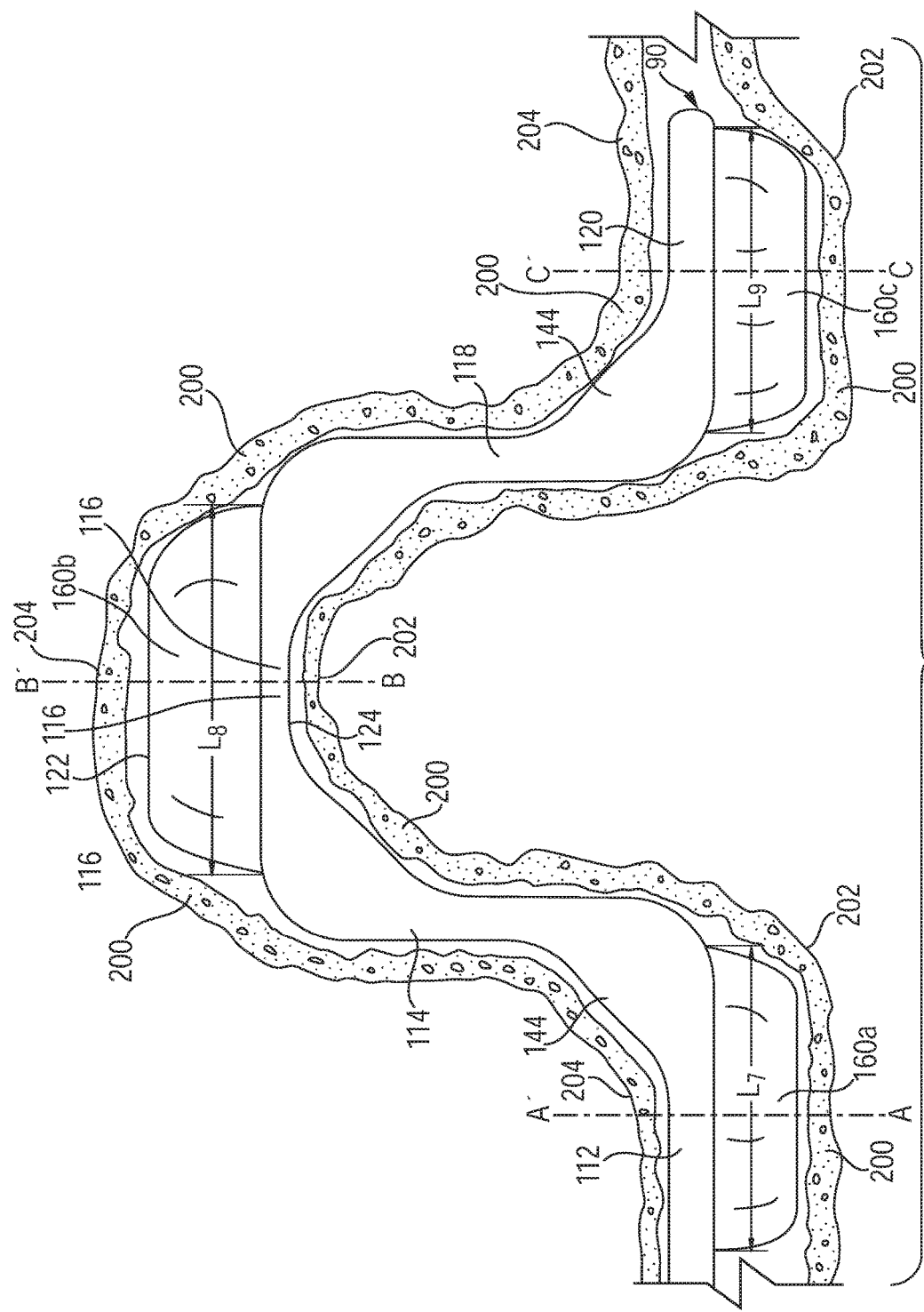
FIG. 10(c) shows distendable section 110 of esophageal displacement and repositioning catheter 10 of FIG. 10(b) with balloons 160a, 160b and 160c in deployed or inflated states positioned in a patient 5's esophagus.
Figure 10F:
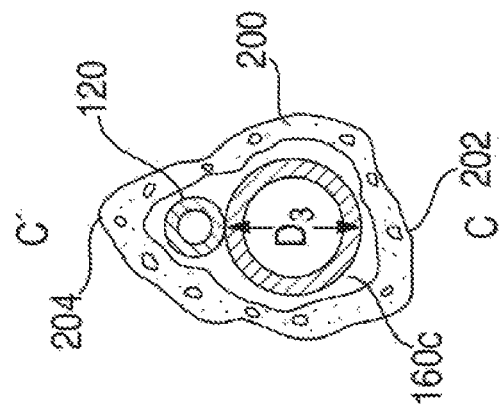
FIGS. 10(d), 10(e) and 10(f) show cross-sectional views of some components and elements of distendable section 110 through sections A-A', B-B' and C-C', respectively, of FIG. 10(c)
Figure 10E:
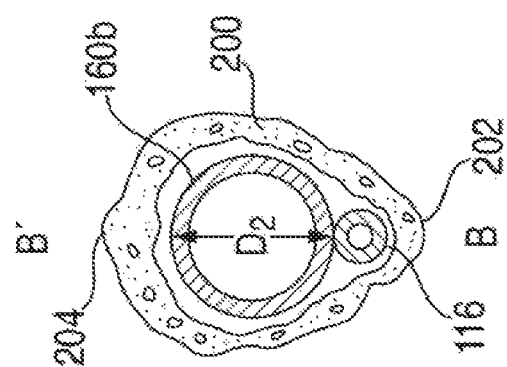
Figure 10D:
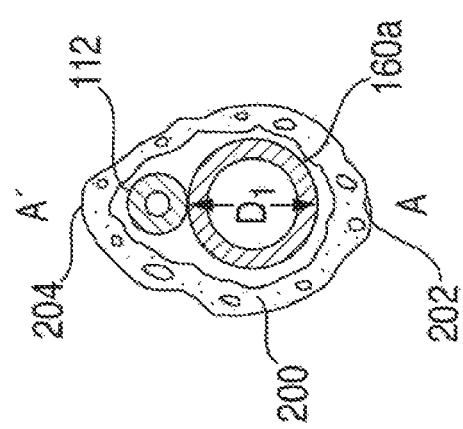

The various dimensions of catheter body 50 and distendable section 110 shown in FIGS. 9(a) through 9(e) illustrate that according to some embodiments catheter body 50 has thin stainless steel walls approximately 0.76 mm thick (with an outer diameter of 4.57 mm, and an inner diameter of 3.81 mm—see FIG. 10(d). Spacing in the axial direction between slots or slits 131 (which can be 0.51 mm, by way of example) in joints 130a, 130b 130c and 130d is reduced relative to spacing in the axial direction between slots or slits 131 in other portions of distendable section 110 or catheter body 50 (which can be 0.64 mm, by way of example). Such variations in slot or slit spacing in the axial direction between adjacent slots or slits permits joints 130a, 130b, 130c and 130d to have increased bendability or flexibility relative to other portions of distendable section 110 and/or catheter body 50. This is required so that distendable section 110 can be deployed and distended with adequate curvature to move a patient's esophagus a safe distance away from ablation site 310.

The various embodiments of catheter 10 shown in FIGS. 9(a) through 9(e) share some characteristics of the embodiments of catheters 10 shown in FIGS. 7(a) through 8(c). For example, the embodiment shown in FIGS. 9(a) through 9(e) features slits or slots cut into or otherwise formed in appropriate portions of thin-walled distendable section 110, which form bendable joints 130a, 130b, 130c and 130d, and that are also configured to impart lesser flexibility or bendability to other portions of catheter body 50. Each such joint comprises one or slits cut through or into the sidewalls of distendable section 110, where the slits or slots are disposed at suitable locations along distendable section 110, and the slits or slots have suitable dimensions of depth, width and length to permit a desired amount, degree and type of bending at joints 130a, 130b, 130c and 130d. Moreover, and in some embodiments, openings, recesses, or slots 150a through 150d are configured to act in conjunction with slots or slits 131 as range limiters at joints 130a, 130b, 130c and 130d so that such joints in distendable section 110 cannot be extended, or are difficult to extend, beyond prescribed ranges of bends (e.g., 85 degrees as shown in FIG. 9(c)). In another embodiment, slots or slits 131 have spacings and widths that permit limited maximum ranges of bending at joints 130a, 130b, 130c and 130d (e.g., about 85 degrees, although other degrees of bending are contemplated, such as about 90 degrees, about 80 degrees, about 70 degrees, about 60 degrees, about 50 degrees, about 45 degrees, about 40 degrees, about 30 degrees, and about 20 degrees).

In some embodiments joints 130a, 130b, 130c and 130d and other portions of distendable section 110 and/or catheter 50, are formed of thin-walled stainless steel or any other suitable metal, metal alloy, plastic or polymer. Thus, and while the disclosure with respect to FIGS. 7(a), 8(a) and FIGS. 9(a) through 9(e) focuses on embodiments of catheter 10 where proximal end 50, catheter body 50, distendable section 110, and distal end 90 of catheter body 50 are formed of thin-walled medical grade stainless steel, it is to be understood that other suitable materials such as polymers and plastics may also be employed to form catheter body 50.

Referring now to FIGS. 2(a) through 9(e), and according some embodiments, esophageal displacement catheter 10 comprises catheter body 50 comprising at least first lumen 40, distal end 90, proximal end 70, and distendable section 110. First lumen 40 extends between at least portions of proximal and distal ends 70 and 90 of catheter body 50. Catheter body 50 is configured to assume a substantially straight configuration along a first longitudinal axis $A_{L1}$, and/or to assume a flexible or limp configuration at least along portions thereof, when catheter body 50 is in a relaxed or non-active configuration. Catheter manipulation mechanism or handle 30 is disposed at or near proximal end 70 of catheter body 50. At least first pulling member 136 is disposed at least partially within catheter 10 and lumen 40, and has a distal portion thereof attached to a portion of catheter body 50 (e.g., first pulling member anchor 134) located at or near distal end 90 of catheter body 50. In one embodiment, pulling member 136 is operably connected to catheter manipulation mechanism 30 such that a user (e.g., a health care provider or physician) can tighten and relax pulling member 136 using, by way of non-limiting example, a pulling member tightening and loosening mechanism 34 forming a portion of or attached to catheter manipulation mechanism 30.

In some embodiments, distendable section 110 comprises a plurality joints, e.g., joints 130a, 130b, 130c and 130d, and is configured to permit distendable section 110 to deflect away from first longitudinal axis $A_{L1}$ and bend substantially within single plane 20 along plurality of joints 130 when pulling member 136 is pulled towards proximal end 70 of catheter body 50. Distendable section 110 and catheter body 50 may further be configured to rotate substantially within single plane 20 when proximal end 70 of catheter body 50 is rotated by a user. Catheter body 50 may be configured such that distendable section 110 is configured to assume a distended configuration suitable for displacing and repositioning esophagus 200 of patient 5 a suitable distance (e.g., at least 20 mm) away from patient's heart 220 when pulling member 136 is in an active or distended position within lumen 40 and catheter body 50 as pulling member 136 is tightened by the user manipulating catheter manipulation mechanism 30. Catheter 10 is configured such that a torsional and rotational force applied to proximal end 70 of catheter body 50 or to catheter manipulation mechanism 30 by the user results in a rotation of proximal end 70 of catheter body 50 through a prescribed angle determined by the user, which in turn results in the torsional force being transmitted efficiently through catheter body 50 and distendable section 110 such that distendable section 110 also rotates substantially through the same prescribed angle when the torsional and rotational force is applied.

In addition, the various embodiments of catheter 10 can feature one or more of the characteristics described below. Distendable section 110 may comprise a plurality of substantially rigid segments (e.g., segments 112, 114, 116, 118 and 120) located in or on distendable section 110. Such segments can be serially connected to one another by flexible joints 130, where each joint 130 is rotatable through a prescribed range of angles. Such segments and joints may be configured to rotate together substantially within single plane 20 when proximal end 70 of catheter body 50 or catheter manipulation mechanism 30 is rotated by a user. One or more of joints 130 may have a range limiter 132 associated therewith. A range limiter 132 may be configured such that joint 130 associated therewith can bend no more than between about 40 degrees and about 90 degrees. Range limiters 132 may be formed a wire, a braided wire, a stranded wire, a synthetic fiber of high tensile strength, or any other suitable material. In one embodiment, plurality of joints 130 may comprise at least first, second, third, fourth, and fifth substantially rigid segments 112, 114, 116, 118 and 120 located in or on the distendable section 110.

In still other embodiments, distendable section 110 may comprise a plurality of slots or slits 131 formed or machined therein, slots or slits 131 being configured to permit distendable section 110 to deflect away from first longitudinal axis $A_{L1}$ and bend substantially within single plane 20 along plurality of joints 130 when pulling member 136 is pulled towards proximal end 70 of catheter body 50, where joints 130 comprise slots or slits 131.

Distendable section 110 and catheter body 50 may be configured to rotate substantially within single plane 20 when proximal end 70 of catheter body 50 or catheter manipulation mechanism 30 is rotated by the user. The plurality of joints 130 may further comprise at least first, second, third and fourth joints 130a, 130b, 130c, 130d, each of the first, second, third and fourth joints 130a, 130b, 130c, 130d together being rotatable through the prescribed angle. At least some of slots or slits 131 may be configured to act as range limiters 132 in distendable section 110. At least one of range limiters 132 may be configured such that the joint 130 associated therewith can bend no more than between about 40 degrees and about 90 degrees.

First pulling member 136 may comprise one or more of a wire, braided wires, and stranded wires. Catheter 10 may further comprise a second pulling member 138 configured to cause elastic and/or deformable sheath 144 disposed at least around an outer diameter of distendable section 110 to engage a trailing edge 202 of patient 5's esophagus 200 when a proximal end of the second pulling member is pulled through the action of the user (e.g., by the user operating catheter manipulation mechanism 30).

Distendable section 110 may comprise a polymeric or any other suitable material. At least portions of catheter body 50 may comprise thin-walled metal tubing. Such metal tubing may comprise stainless steel or alloys thereof. In some embodiments, the outside diameter of the metal tubing may range between about 2 mm and about 10 mm.

One or more temperature sensors, ultrasonic transducers, navigation sensors, and/or radio opaque markers may be disposed in distendable section 110 or other portions of catheter body 50. At least one mark may be disposed along catheter body 50 that is indicative of at least one of a first position of distal end 90 of catheter body 50 in patient 5's esophagus 200 and a second position of distendable section 110 in patient 5's esophagus 200.

FIGS. 10(a) through 10(f) show yet another embodiment of distendable section 110 of catheter 10, where balloons 160a, 160b and 160c are attached to or form a portion of distendable section 110. Balloons 160a, 160b and 160c are configured to further push patient 5's esophagus 200 a suitable and safe distance D2 away from the patient's heart 220 and the source of heat 310 used to ablate the patient's heart of pulmonary vein during an atrial ablation procedure.

In FIG. 10(a), distendable section 110 is shown in a distended or active position, but with balloons 160a, 160b and 160c not in expanded or deployed positions. In FIGS. 10(b) and 10(c), balloons 160a, 160b and 160c are shown in their inflated or fully deployed states. As illustrated in FIG. 10(c), balloons 160a, 160b and 160c push the patient's esophagus 200 further away from heart 220 than do the embodiments of distendable section 110 shown in preceding Figures. As shown in FIG. 10(c), and according to some embodiments, balloons 160*a*, 160*b* and 160(*c*) may be characterized by lengths L7, L8 and L9, respectively.

Balloons 160*a* through 160*c* may be inflated using air or a suitable fluid that is injected through catheter body 50 and suitable lumen(s) and/or tube(s) contained within or external to catheter body 50, where the air or fluid is injected into (and/or withdrawn from) the balloons under the control of a health care provider using control mechanism 50. Such air or fluid carrying lumens or tubes may be disposed outside and along catheter body 50, or may be internal to catheter body 50. By way of non-limiting example, balloons 160*a* through 160*c* may be formed of suitably expandable materials such as silicone, rubber, latex, MYLAR®, nylon, PTA, PTFE, polyurethane polyimide, polyurethane, polyethylene, polyimide, polyetheretherketone, polyethylene terephthalate, polypropylene, and/or fluoroplastic. In some embodiments, balloons 160*a* through 160*c* possess a flexural modulus of between about 90 MPa and about 500 MPa.

As shown in FIGS. 10(*d*) through 10(*f*), balloons 160*a* through 160*c* may have diameters D1, D2 and D3, which in some embodiments can range between about 8 mm and about 40 mm, between about 10 mm and about 25 mm, and between about 12 mm and about 16 mm. Other diameters of balloons 160 a through 160*c* are also contemplated. For purposes of providing simplified views, note that FIGS. 10(*d*) through 10(*f*) do not illustrate all elements of a working distendable section 110, such as pulling members 136 and/or 138, outer layer or covering 144, and so on.

The number of balloons attached to or forming a portion of distendable section 110 can also vary, such as one balloon, two balloons, four balloons, and other numbers of balloons. Balloons 160 may be disposed on upper, lower of side portions of distendable section 110 and/or catheter body 50. Balloons 160*a* through 160*c* must possess sufficient burst strength not to rupture or break when deployed inside a patient and inflated or enlarged, and should be configured to withstand, by way of non-limiting example, pressures ranging between about 0.2 atmospheres (2.9 psi) and 1.0 atmosphere (14.7 psi). Balloons 160*a*, 160*b* and 160*c* may also be configured to assume spherical, cylindrical, conically tapering and other suitable shapes. Balloons 160*a* through 160*d* may also be positioned on catheter body 50 such that outer layer or covering 144 is positioned over or on top of such balloons; such embodiments can permit eased routing of air and/or fluid supply to balloons 160*a* through 160*d*.

Balloons 160*a*, 160*b* and 160*c* may be formed by heating a tubular material within a mold, heat-sealing thin sheets to one another, or using a blow-molding process. In a blow-molding process, a thermoplastic material such as nylon, polyurethane, or polycarbonate is extruded or formed into a hollow, tube-like shape (parison) and is subsequently heated and pressurized, usually with air, inside a hollow mold having a shape to form the final outer dimensions of the balloon.

Figure 11B:
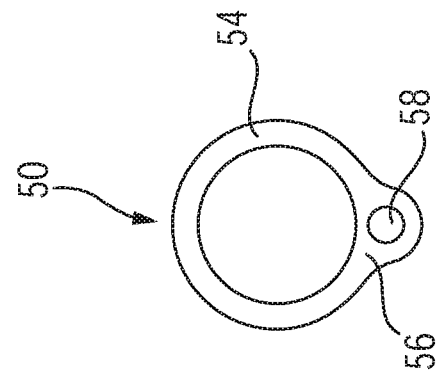
FIGS. 11(a) and 11(b) show side and end cross-sectional views of catheter body 50 and sensor coupling mechanism 56.
Figure 11A:
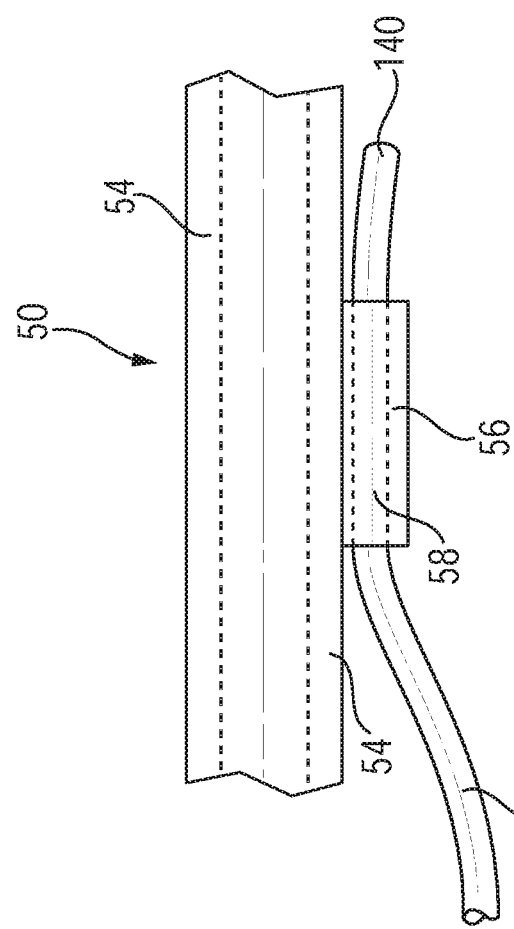

FIGS. 11(*a*) and 11(*b*) show side cross-sectional and end cross-sectional views of portions of catheter body 50 having sensor coupling mechanism or holder 56 attached thereto. As shown, sensor 140, which by way of example may be any suitable sensor described above (such as a temperature sensor, a navigation sensor, an acoustic sensor, or a HIFU sensor) attaches to catheter body 50 by sliding through and frictionally engaging recess 58 of sensor coupling mechanism 56 (which extends outwardly from catheter body 54). Other means of coupling and attaching sensors to the outside of catheter 50 are contemplated, such as moldings, bands, recesses, clips, screws, tape, adhesive, clamps, and so on. Sensor coupling mechanism 56 can be configured to permit off-the-shelf embodiments of sensors to be readily and quickly attached to catheter 10.

Figure 12:
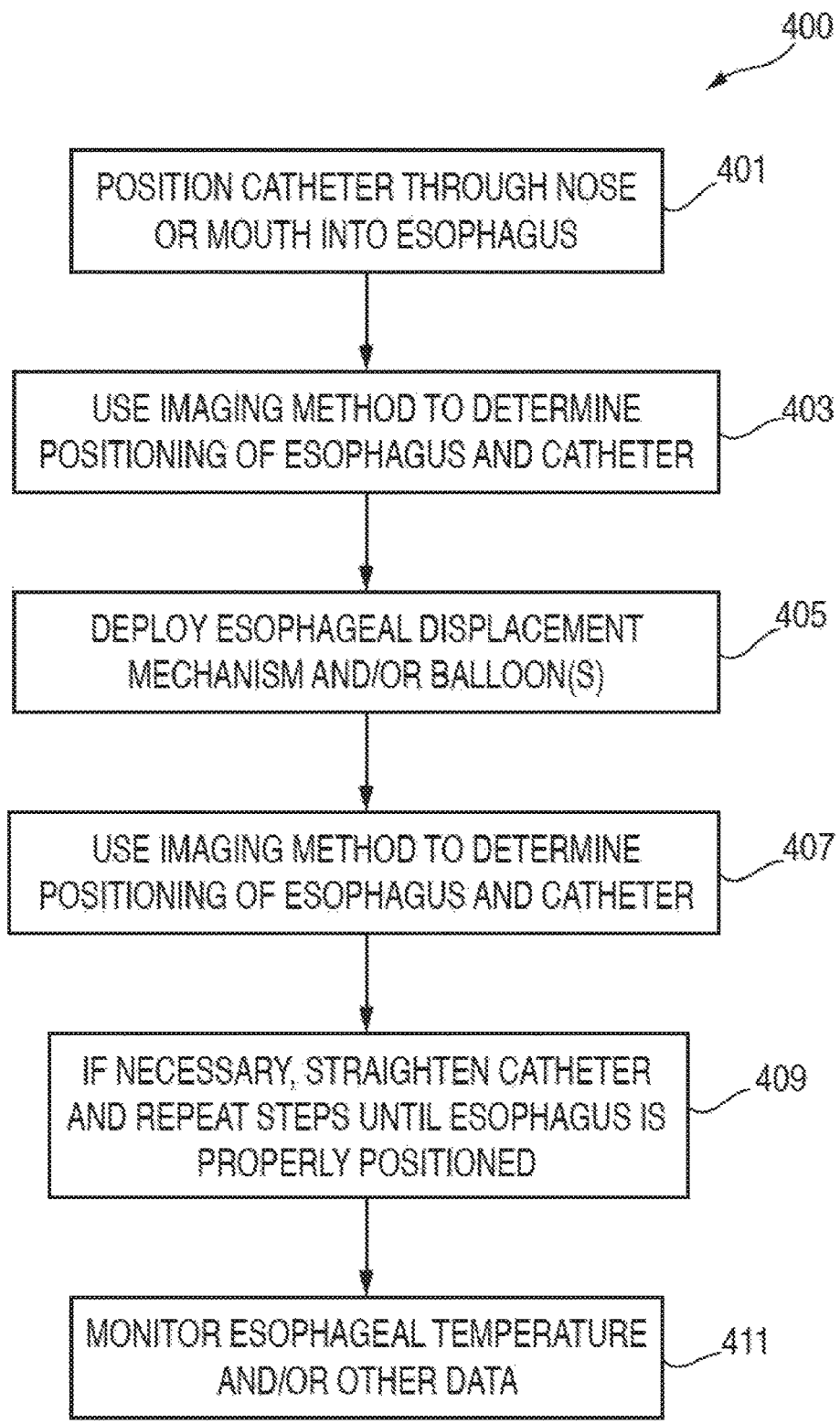
FIG. 12 shows one embodiment of method 400 for using an esophageal displacement and repositioning catheter.

FIG. 12 shows one embodiment of a method 400 for using an esophageal displacement and repositioning catheter 10. In FIG. 12, catheter 10 is first positioned through patient 5's nose or mouth at step 401. At step 403, a suitable imaging method is preferably, although not necessarily, employed to determine the position of catheter 10 and distendable section 110 in esophagus 200 relative to heart 220. If catheter 10 is determined to be in an appropriate position in patient 5's esophagus relative to heart 220, at step 405 distension mechanism 110 and/or balloons 160 of catheter 10 are deployed to reposition esophagus 200 away from heart 220 and/or ablation tip 310. At step 407, a suitable imaging method is preferably once again employed to determine the position of catheter 10 and distendable section 110 in esophagus 200 relative to heart 220. If necessary, catheter 10 is straightened at step 409 and repositioned in esophagus 200. Temperature or other data can be acquired from catheter 10 in step 411 or in any of the other steps of method 400 (as described above).

Many variants, permutations and combinations of method 400 described above are contemplated, including methods where certain of the above-described steps are eliminated, steps practiced in an order different from that described above, or other steps are added.

In addition to the systems, devices, and components described above, it will now become clear to those skilled in the art that various methods associated therewith are also disclosed and contemplated, such as methods of manufacturing and modifying esophageal repositioning and displacement catheters.

Various aspects or elements of the different embodiments described herein may also be combined to implement esophageal repositioning and displacement techniques.

The foregoing outlines features of several embodiments so that those skilled in the art may better understand the detailed description set forth herein. Those skilled in the art will now understand that many different permutations, combinations and variations of esophageal repositioning and displacement catheters 10 fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems in the use of esophageal repositioning and displacement catheters.

I claim:

1. An esophageal displacement catheter, comprising:
   a catheter body having a longitudinal axis associated therewith, the catheter body comprising a distal end, a proximal end, at least one lumen, and a distendable section having sidewalls, the lumen extending between at least portions of the proximal and distal ends, the catheter body being configured to assume an at least partially flexible or limp configuration along at least portions of the longitudinal axis when the catheter body is in a relaxed or non-active configuration;

a catheter manipulation mechanism disposed at or near the proximal end of the catheter body;

at least a first pulling member disposed at least partially within the catheter and the lumen, the first pulling member comprising a distal portion operably connected to or near a distal end of the catheter body and a proximal portion operably connected to the catheter manipulation mechanism such that a user can tighten and relax the pulling member using the catheter manipulation mechanism, and at least one elastic flexible deformable or distendable member, sheath, layer or covering disposed over at least portions of the distendable section;

wherein the distendable section comprises a plurality of substantially rigid sections interconnected by a plurality of joints disposed along the distendable section, the joints and substantially rigid segments being configured to permit the distendable section to deflect away from the longitudinal axis and assume a distended configuration when the first puffing member is pulled or retracted sufficiently far towards the proximal end of the catheter body using the catheter manipulation mechanism, the distendable section further being configured such that portions of the first pulling member extend sufficiently far away from the joints when the first pulling member is in a retracted position to permit the distendable section to assume a deployed and distended configuration, and the at least one flexible deformable or distendable member, sheath or covering is configured to be disposed over and cover the portions of the first pulling member extending away from the joints when the distendable section is the deployed and distended configuration, the catheter being configured to displace and reposition an esophagus of a patient at least 20 mm away from the patient's heart when the distendable section is in the deployed and distended configuration.

2. The esophageal displacement catheter of claim 1, wherein the distendable section further comprises a plurality of openings, recesses, slots or slits disposed in the sidewalls of the catheter body at or near at least some of the joints such that the portions of the first pulling member extending away from the joints are disposed through the openings, recesses, slots or slits when the distendable section is in the deployed and distended configuration.

3. The esophageal displacement catheter of claim 1, wherein distendable section comprises at least three, four or five substantially rigid sections.

4. The esophageal displacement catheter of claim 1, wherein the distendable section is configured to form a compound bend substantially within a single plane along the plurality of joints when the pulling member is pulled towards the proximal end of the catheter body.

5. The esophageal displacement catheter of claim 4, wherein the distendable section and the catheter body are further configured to rotate substantially within the single plane when the proximal end of the catheter body is rotated by a user.

6. The esophageal displacement catheter of claim 5, wherein the catheter is configured such that a torsional and rotational force applied to the proximal end of the catheter body or the catheter manipulation mechanism by the user results in the torsional force being transmitted to the distal end of the catheter.

7. The esophageal displacement catheter of claim 1, wherein each substantially rigid segment is rotatable through a prescribed range of angles.

8. The esophageal displacement catheter of claim 1, wherein at least one of the joints has a range limiter associated therewith.

9. The esophageal displacement catheter of claim 1, wherein a first length L1 between the proximal and distal ends of the catheter body ranges between about 200 mm and about 600 mm.

10. The esophageal displacement catheter of claim 1, wherein a second length L2 of the distendable section ranges between about 100 mm and about 300 mm.

11. The esophageal displacement catheter of claim 1, wherein a third length L3 of the distendable section ranges between about 80 mm and about 250 mm.

12. The esophageal displacement catheter of claim 1, wherein a first height H1 of the distendable section ranges between about 40 mm and about 140 mm.

13. The esophageal displacement catheter of claim 1, wherein a second height H2 of the distendable section ranges between about 20 mm and about 80 mm.

14. The esophageal displacement catheter of claim 1, further comprising a second pulling member configured to cause portions of the at least one elastic flexible deformable or distendable member, sheath, layer or covering to engage a trailing edge of the patient's esophagus when a proximal end of the second pulling member is retracted.

15. The esophageal displacement catheter of claim 1, wherein the at least one elastic flexible deformable or distendable member, sheath, layer or covering comprises one or more of a flexible, stretchable, distendable and retractable mesh, or a flexible, stretchable, distendable and retractable silicone-based material, a medical-grade silicone, a rubber silicone material, a latex-based material, latex, a rubber-based material, rubber, a rubber latex material, a urethane-based material, a polyurethane-containing material, a flexible polyethylene-containing material, a polyethylene terephthalate (PET)-containing material, a polyisoprene-containing material, polypropylene, fluoroplastic, a polymer, an elastomer, a thermoplastic elastomer, or a combination or mixture of the foregoing.

16. The esophageal displacement catheter of claim 1, wherein at least portions of the catheter body comprise thin-walled metal tubing.

17. The esophageal displacement catheter of claim 16, wherein the metal tubing comprises stainless steel or alloys thereof.

18. The esophageal displacement catheter of claim 1, wherein a diameter of the catheter body ranges between about 2 mm and about 10 mm.

19. The esophageal displacement catheter of claim 1, further comprising one or more temperature sensors disposed in the distendable section.

20. The esophageal displacement catheter of claim 1, further comprising one or more ultrasonic transducers disposed in the distendable section.

21. The esophageal displacement catheter of claim 1, further comprising one or more navigation sensors disposed in the distendable section.

22. The esophageal displacement catheter of claim 1, further comprising one or more radio opaque markers disposed in the distendable section.

23. The esophageal displacement catheter of claim 1, further comprising one or more balloons disposed in the distendable section, the balloons being configured to enlarge controllably a diameter of the distendable section.

24. A method of displacing a portion of an esophagus of a patient away from the patient's heart with an esophageal displacement catheter, the catheter comprising a catheter body having a longitudinal axis associated therewith, the catheter body comprising a distal end, a proximal end, at least one lumen, and a distendable section having sidewalls, the lumen extending between at least portions of the proximal and distal ends, the catheter body being configured to assume an at least partially flexible or limp configuration along at least portions of the longitudinal axis when the catheter body is in a relaxed or non-active configuration, a catheter manipulation mechanism disposed at or near the proximal end of the catheter body, at least a first pulling member disposed at least partially within the catheter and the lumen and comprising a distal portion operably connected to or near a distal end of the catheter body and a proximal portion operably connected to the catheter manipulation mechanism such that a user can tighten and relax the pulling member using the catheter manipulation mechanism, and at least one elastic flexible deformable or distendable member, sheath, layer or covering disposed over at least portions of the distendable section, the distendable section comprising a plurality of substantially rigid sections interconnected by a plurality of joints disposed along the distendable section, the joints and substantially rigid segments being configured to permit the distendable section to deflect away from the longitudinal axis and assume a distended configuration when the first pulling member is retracted or pulled sufficiently far towards the proximal end of the catheter body using the catheter manipulation mechanism, the distendable section further being configured such that portions of the first pulling member extend sufficiently far away from the joints when the first pulling member is in a retracted position to permit the distendable section to assume a deployed and distended configuration, and the at least one flexible deformable or distendable member, sheath or covering is configured to be disposed over and cover the portions of the first pulling member extending away from the joints when the distendable section is the deployed and distended configuration, the catheter being configured to displace and reposition an esophagus of a patient at least 20 mm away from the patient's heart when the distendable section is in the deployed and distended configuration, the method comprising:

inserting the distal end of the catheter body in the patient's nose or mouth;

inserting and positioning the distal end of the catheter into the patient's esophagus, and causing the first pulling member to retract in the direction of the proximal end of the catheter body such that the distendable section is deployed, the distendable section assumes the distended configuration, and the distendable section positions the patient's esophagus at least 20 mm away from the patient's heart.

25. The esophageal displacement method of claim 24, further comprising medically imaging the position of the catheter in the patient's esophagus.

26. The esophageal displacement method of claim 25, further comprising re-positioning the catheter in the patient's esophagus based on the imaging results.

27. The esophageal displacement method of claim 24, further comprising monitoring a temperature of a trailing edge of the patient's esophagus using one or more temperature sensors located in the distendable section of the catheter.

* * * * *